United States Patent [19]

Pitzele et al.

[11] Patent Number: 4,760,180
[45] Date of Patent: Jul. 26, 1988

[54] N-TERMINALLY SUBSTITUTED DIPEPTIDE AMIDES

[75] Inventors: Barnett S. Pitzele, Skokie; Donald W. Hansen, Jr., Chicago; Robert W. Hamilton, Wilmette; Daniel R. Pilipauskas, Glenview; Michael Clare, Skokie, all of Ill.

[73] Assignee: G. D. Searle & Co., Chicago, Ill.

[21] Appl. No.: 882,795

[22] Filed: Jul. 14, 1986

Related U.S. Application Data

[63] Continuation-in-part of Ser. No. 829,241, Feb. 14, 1986, abandoned, which is a continuation-in-part of Ser. No. 765,881, Aug. 14, 1985, abandoned.

[51] Int. Cl.$^4$ ............................................. C07C 103/20
[52] U.S. Cl. ....................................................... 564/157
[58] Field of Search ........................ 530/302; 514/19; 564/157

[56] References Cited

U.S. PATENT DOCUMENTS

| | | | |
|---|---|---|---|
| 4,127,535 | 11/1978 | Coy et al. | 530/302 |
| 4,316,892 | 2/1982 | Jones | 530/302 |
| 4,407,746 | 10/1983 | Mazur et al. | 530/302 |
| 4,579,841 | 4/1986 | Stewart et al. | 514/19 |
| 4,603,121 | 7/1986 | Hansen, Jr. et al. | 530/302 |

Primary Examiner—Delbert R. Phillips
Attorney, Agent, or Firm—Frank P. Grassler; Paul D. Matukaitis

[57] ABSTRACT

This invention encompasses compounds of the formula

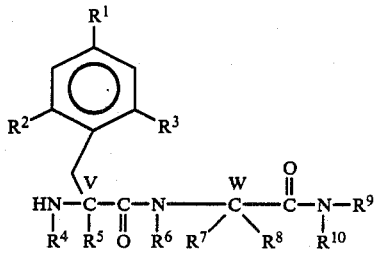

and the pharmaceutically acceptable acid addition salts thereof wherein $R^1$ is lower alkoxy or —O—$(CH_2)_n$-phenyl where the phenyl may be optionally substituted with halogen, —$NO_2$, —CN, —$NH_2$ or lower alkyl wherein n is 1 to 4; $R^2$ and $R^3$ represent lower alkyl, halogen, lower alkoxy or one of $R^2$ or $R^3$ is hydrogen and the other is lower alkyl, lower alkoxy, or halogen; $R^4$, $R^5$, $R^7$, $R^8$, and $R^9$ represent hydrogen or lower alkyl, $R^6$ represents hydrogen, lower alkyl, lower alkenyl, or —$(CH_2)_m$-cycloalkyl wherein m is 1 to 4 and the cycloalkyl has 3 to 8 carbon atoms; $R^{10}$ is —$(CH_2)_p$-phenyl wherein p is 1 to 4; and v represents an asymmetric carbon that may be racemic or have the D or L Configuration; w represents an asymmetric carbon when $R^7$ and $R^8$ are not the same that may be racemic or have the D or L configuration. This invention also encompasses compounds where $R^1$ is hydroxy, provided at least one of $R^4$, $R^5$, $R^6$ or $R^9$ is lower alkyl. The compounds of this invention are useful analgesic agents.

26 Claims, No Drawings

N-TERMINALLY SUBSTITUTED DIPEPTIDE AMIDES

This is a continuation-in-part of abandoned Ser. No. 829,241 filed Feb. 14, 1986 which is a continuation-in-part Ser. No. 765,881 filed Aug. 14, 1985, now abandoned.

FIELD OF THE INVENTION

The present invention relates to novel dipeptide amides. In particular, it provides novel dipeptide derivatives of Formula 1 which are useful as analgesic or antihypertensive agents.

BACKGROUND OF THE INVENTION

In 1975, a pentapeptide, methionine enkephalin, was reported by Hughes et al., Nature, 258, 577 (1975). This peptide is found in many areas of the brain where it appears to act as a neurotransmitter or neuromodulator in a central pain-suppressant system. The natural peptide binds stereospecifically to partially purified brain opiate receptor sites, see for example, Bradberry et al., Nature, 260, 793 (1976). The natural peptide is also highly active in bioassays for opiate activity but exhibits only weak, fleeting analgesic activity when injected directly into the brain of the rat, see for example, Belluzi et al., Nature, 260, 625 (1976)

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., "Peptide Chemistry 1981,": C5-70, Protein Research Foundation, Osaka, Japan (1982), disclosed the synthesis and activity of short chain enkephalin-like peptides, among them tripeptide and dipeptide alkylamides such as N-methyl tyrosine (D) methionine sulfoxide glycine-methylphenethylamide (2) and tyrosine-(D) methionine sulfoxide phenylpropylamide (3).

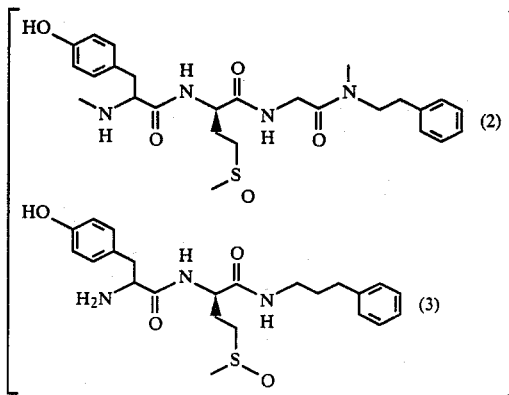

Vavrek, et al., Peptides 2, 303, 1981 disclosed analogs of enkephalin, among them the dipeptide tyrosine-D-alanine-phenylpropylamide (Tyr-(D) Ala-PPA) (4).

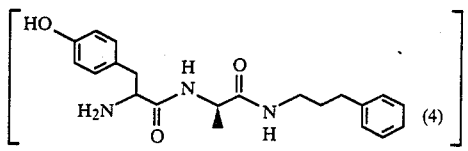

The compounds of this invention have unexpected and surprisingly superior properties when compared to the Vavrek compound. The present invention provides new enkephalin derivatives which show improved potency as analgesic agents by both oral and parenteral routes of administration. Additionally, U.S. Pat. No. 4,316,892 relates to certain derivatives of methionine enkephalin derivatives useful as analgesic agents.

SUMMARY OF THE INVENTION

This invention encompasses analgesic agents of the formula

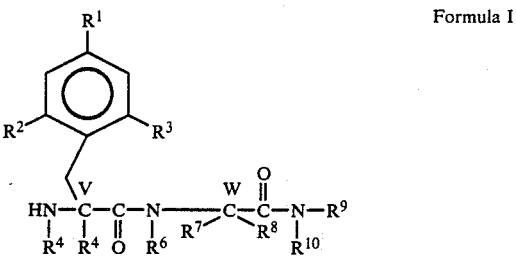

Formula I and the pharmaceutically acceptable acid addition salts thereof wherein $R^1$ is lower alkoxy or —O—$(CH_2)_n$—phenyl Where the phenyl may be optionally substituted with halogen, —$NO_2$, —CN, —$NH_2$ or lower alkyl wherein n is 1 to 4; $R^2$ and $R^3$ represent lower alkyl, halogen, lower alkoxy or one of $R^2$ or $R^3$ is hydrogen and the other is lower alkyl, lower alkoxy, or halogen; $R^4$, $R^5$, $R^7$, $R^8$, and $R^9$ represents hydrogen, lower alkyl, lower alkenyl, or —$(CH_2)_m$—cycloalkyl wherein m is 1 to 4 and the cycloalkyl has 3 to 8 carbon atoms; $R^{10}$ is —$(CH_2)_p$—phenyl wherein p is 1 to 4; and v represents an asymmetric carbon that may be racemic or have the D or L Configuration; w represents an asymmetric carbon when $R^7$ and $R^8$ are not the same that may be racemic or have the D or L configuration. This invention also encompasses compounds where $R^1$ is hydroxy, provided at least one of $R^4$, $R^5$, $R^6$ or $R^9$ is lower alkyl.

A preferred embodiment of the invention are compounds of the formula

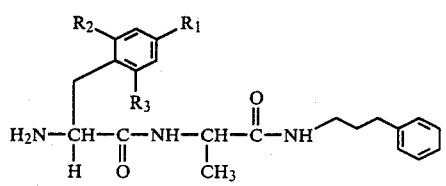

and the pharmaceutically acceptable acid addition salts thereof wherein both $R^2$ and $R^3$ are methyl, hydrogen, or chloro; and $R^1$ is —O—$(CH_2)_n$—phenyl with the phenyl optionally substituted with halogen, —$NO_2$, —CN, —$NH_2$, or lower alkyl wherein n is 1 to 4. By lower alkyl is meant straight or branched chain alkyl having 1 to 6 carbon atoms such as, methyl, ethyl, propyl, isopropyl, butyl, isobutyl, tertiary butyl, pentyl, hexyl and isomers thereof.

By lower alkoxy is meant alkoxy containing 1 to 6 carbon atoms and having the above lower alkyl moieties. Lower alkenyls are the above lower alkyls having one double bond.

Optionally substituted phenyl means phenyl substituted in the ortho, meta, or para position with one or more of the specified groups.

DESCRIPTION OF THE SPECIFIC EMBODIMENTS

The compounds described in this invention and illustrated in Examples 1–68 are synthesized by either of two procedures illustrated in Scheme I Route A and Scheme II Route B. Many of the compounds can be prepared by either route with the principal difference being the reaction sequence.

Route A in Scheme I and Route B in Scheme II illustrate two methods for making compounds of this invention. In Route A a blocked amino acid derivative X is reacted with a dialkyl amine XI by mixed anhydride coupling and the blocking group Z is removed by $H_2/Pd$ reduction to provide amide XII. A blocked tyrosine derivative XIII is reacted with amide XII by the mixed anhydride method to provide XIV which is separated into diastereomers, which are separately deblocked to provide compounds of formula I.

In Route B Scheme II the ester of the amino acid derivative is coupled with XIII by mixed anhydride coupling to provide ester XVI. This ester XVI is separated into diastereomer. For example, if XV is a D amino acid derivative and XIII is a DL tyrosine derivative, the DD and LD diastereomers are provided. The appropriate dialkylamine is then coupled to the separated diastereomer of XVII, and the product is deblocked to provide the compounds of Formula I.

In Schemes I and II, BOC refer to tertiary butoxy carbonyl and $R^1$ through $R^{10}$ are as previously defined. Z may be BOC or carbobenzoxy or other suitable blocking groups.

Diastereomers are separated by standard techniques such as crystalization or column chromatography.

SCHEME I
ROUTE A

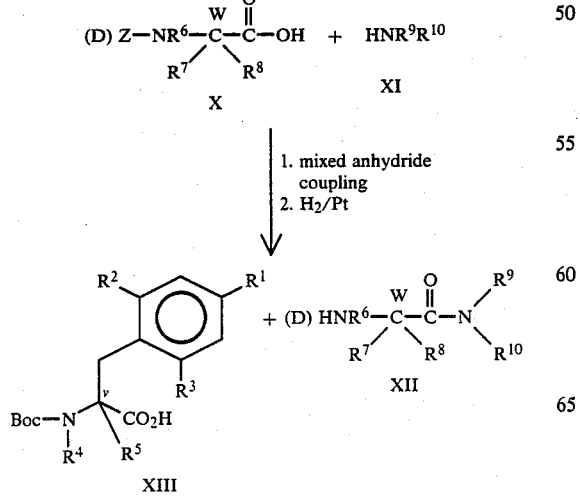

SCHEME I
ROUTE A

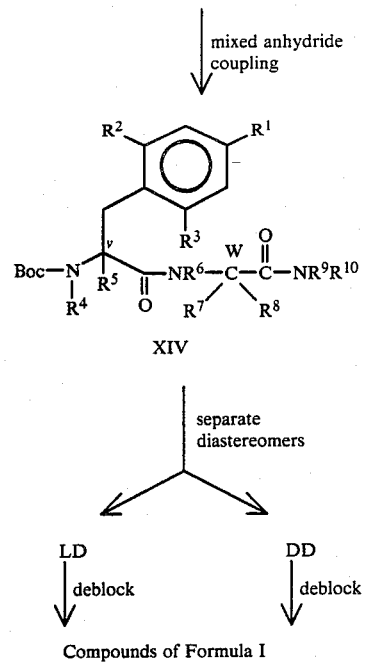

SCHEME II
ROUTE B

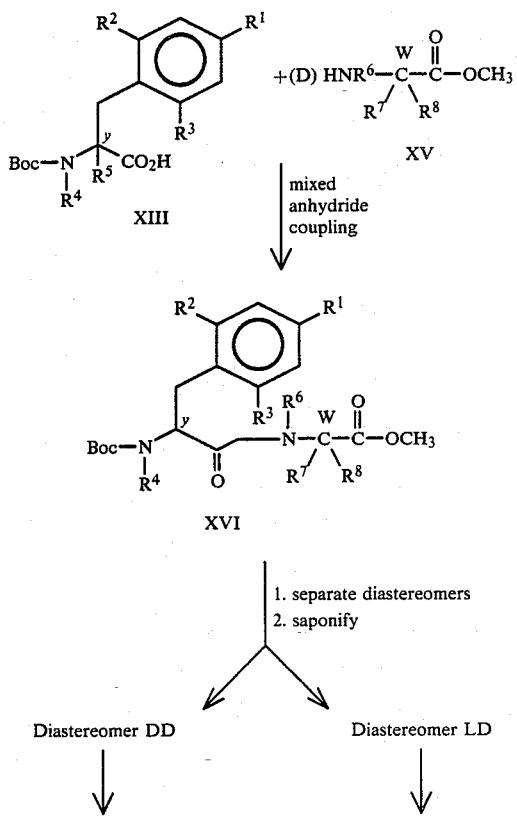

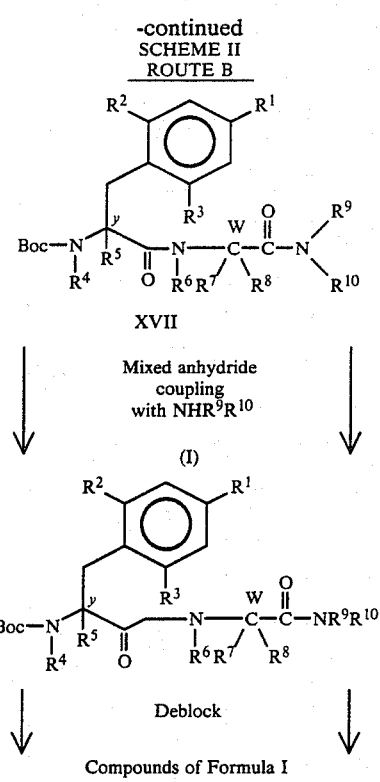

-continued
SCHEME II
ROUTE B

XVII

Mixed anhydride coupling with NHR⁹R¹⁰

(I)

Deblock

Compounds of Formula I

The analgesic activity for the compounds of the present invention is illustrated by their activity in the writhing test. The analgesic activity of the representative compounds was compared with that of a disclosed analog of enkephalin, tyrosine-(D)-alanine- phenylpropylamide.

Writhing assay. Male Charles River albino mice (CD-1/HAM/1LR) weighing between 20 and 30 grams were used. Thirty minutes after subcutaneous or intragastric administration of the test compound (0.1 ml/10 gram body weight), 0.025(w/v) phenylbenzoquinone was injected intraperitoneally (0.1 ml/10 gram body weight). Five minutes later, each mouse was placed in a large glass beaker and the number of writhes that occurred in the subsequent ten minutes is counted. A writhe consisted of dorsoflexion of the back, extension of the hindlimbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the treatment group was significantly less than the number of writhes in the saline treated control group as determined by a one-way analysis of variance. If the initial test dose of 10 mg/kg inhibited writhing in greater than 6 of IO mice, the effect of additional doses was evaluated and an $ED_{50}$ value was calculated using a maximum likelihood function.

Opiate Binding Assay. The test compounds were evaluated for their ability to displace the binding of ³H-Naloxone to opiate receptors isolated from rat brain. Male rats [Crl CD(SD)BR] obtained from Charles River Laboratories (Portage, Mich.) were sacrificed by cervical dislocation. A purified homogenate of receptor membranes was prepared from the brains according to the method described by Chang and Cuatrecasas. (K.-J. Chang and P. Cuatrecasas. Multiple Opiate Receptors: Enkephalins And Morphine Bind To Receptors Of Different Specificity. *J. Biol. Chem.* 254, 2610–2618 (1979).) The brains were homogenized in 10 volumes of 0.32M sucrose and centrifuged twice at 6,000xg for 15 minutes. Following centrifugation of the supernatants at 40,000xg for 30 minutes, the pellets were resuspended in 5mM Tris-HCl and then centrifuged at 6,000xg. The supernatant was centrifuged at 40,000xg. This resuspended pellet (5mM Tris HCl) was centrifuged twice. The final pellet was resuspended in 2 volumes of 50 mM tris HCl (pH 7.4). The homogenate was assayed for protein content according to the method of Itzhaki and Gill. (R. F. Itzhaki and D. M. Gill. A Micro-Biuret Method for Estimating Proteins. *Anal. Biochem.* 9, 401–410 (1964).

The binding of the test compounds to the receptor membrane preparation was measured using a modification of the method of Pert and Snyder. (C. B. Pert and S. H. Snyder. Properties of Opiate-Receptor Binding in Rat Brain. *Proc. Natl. Acad. Sci.* 70, 2243–2247 (1973). The receptor assay was run using final concentrations of 1 nM ³-H-Naloxone and 0.5 mg/ml of homogenate protein.

Levorphanol ($1\times10^{-5}$M) was used as the displacer for non-specific binding. Final concentration of the test compounds was $10^{-5}$M. The assay was run in 0.05M tris HCl (pH 7.4). Total assay volume was 1.0 ml.

Samples were incubated at 25° C. for 60 min., filtered over Whatman GF/C glass fiber filters and rinsed twice with 4 ml washes of ice-cold buffer. The filters were air-dried at 50° C. for 30 minutes. After drying, 10 ml of PCS was added to the vial and the radioactivity determined using a tracor analytic Mark III liquid scintillation counter with a counting efficiency of 48.

The $IC_{50}$ value, the concentration of the test compounds which inhibited ³H-Naloxone specific binding to the opiate receptor by 50, were obtained from log-logit plots of concentration-response curves.

The compounds can be administered in such oral dosage forms as tablets, capsules, pills, powders, granules, suspensions, or solutions. They may also be administered rectally or vaginally, in such forms as suppositories or bougies. They may also be introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula 1 can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula 1 is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. The accompanying descriptions and figures are used to illustrate two of the possible methods used to prepare the compounds of this invention.

All NMR's are proton magnetic resonance of 80 MHz in DMSO$_{db}$ with chemical shifts in $f$ expressed as ppm from an internal TMS standard. All optical rotations are in Methanol.

Solvent stripping was under reduced pressue at or below 35°.

EXAMPLE 1

N-[(1,1-dimethylethoxy)carbonyl]-0,2,6-trimethyl-DL-tyrosine

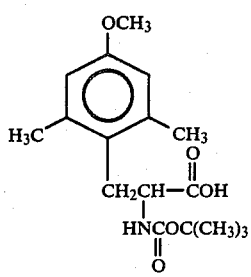

Boc-2,6-dimethyltrosine (3.0 g, 9.70 mmol) was stirred with methyl iodide (6.88 g, 48.5 mmol) and potassium carbonate (5.36 g, 38.8 mmol) in dimethylformamide (DMF) (50 ml) for 17 hr in a 100 ml round-bottom single necked flask, protected from moisture with a drying tube. The reaction mixture was partitioned between water and diethyl ether. The aqueous phase was washed twice with ether and the organic fractions were combined, dried (MgSO$_4$), filtered, and stripped to a white solid. Used as is NMR: methoxy singlets at $f$ 3.51 and 3.66.

0-Methyl-Boc-2,6-dimethyltyrosine methyl ester (directly from the above reaction, 9.7 mmol if yield was quantitative) was dissolved in methanol (70 ml) and cooled in an ice bath. A solution of NaOH (3.1 g, 77.6 mmol) in water (20 ml) was added. The mixture was stirred for three hours. A TLC in (1:1 Skelly B: Ethyl acetate (EtoAc) on silica slides showed that the reaction was complete. A solution of KHSO$_4$ (10.6 g, 77.6 mmol) in water (75 ml) was added. The mixture was stripped to a lower volume to remove methanol, and extracted twice with CH$_2$Cl$_2$ (methylene chloride). The organic fractions were combined, dried (MgSO$_4$), filtered, and stripped. The weight was 2.6 g. NMR: one methoxy singlet only, at $f$ 3.66.

EXAMPLE 2

0,2,6-trimethyl-DL-tyrosyl-N-(3-phenylpropyl)-D-alaninamide, monohydrochloride

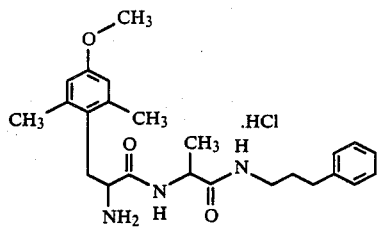

A 100 ml 3-necked round bottom flash was set up with a magnetic stirrer, thermometer, dropping funnel (pressure equilibrating), and a y-tube. The y-tube was connected to a N$_2$ inlet and a drying tube outlet. The system was flushed with N$_2$. O-methyl-Boc-2,6-dimethyltyrosine (2.52 g, 7.79 mmol) in CH$_2$Cl$_2$ (30 ml) was introduced. 5A molecular sieves (2 g, 8–12 mesh) were added. The reaction mixture was cooled to −15°, and N-methylmorpholine (0.86 ml, 7.79 mmol) was added. The reaction mixture was allowed to warm to +5°, and then cooled to −60°. Isobutylchloroformate (1.02 ml, 7.79 mmol) was added. The flask was then immersed in an ice bath (0°), and the reaction was run at 0° for 30 min. The flask was then immersed in a dry ice-acetone bath, and cooled to −70°. N-methylmorpholine (0.86 ml, 7.79 mmol) was then added, followed by the dropwise addition of D-alanylphenylpropylamide hydrochloride (1.89 g, 7.79 mmol) in CH$_2$Cl$_2$ (10 ml), keeping the reaction temperature at or below −55°. After the addition was complete, the reaction mixture was allowed to warm to room temperature, and stirring was continued another 1.5 hr. The reaction mixture was then filtered. The filtrate was washed with 0.5M KHSO$_4$. The resulting aqueous layer was then washed with fresh CH$_2$Cl$_2$. The organic fractions were combined, dried (MgSO$_4$), filtered and stripped to a hard foam (4.51 g). This material was purified by column chromatography on woelm silica. The eluent was CH$_2$Cl$_1$:Ethanol (2B):NH$_4$OH conc (98:2:0.1).

The resulting material (4.45 g) was dissolved in glacial acetic acid (50 ml) and treated with 6.8N HCl in dioxane (12 ml). After 1.5 hr of reaction at room temperature, the mixture was stripped to a syrup. The syrup was dissolved in methanol, filtered, stripped, and triturated repeatedly with diethyl ether. The resulting solid was dried in a vacuum desiccator to give the product As the hydrochloride hemihydrate. Calcd for C$_{24}$H$_{33}$N$_3$O$_3$. HCl ½ H$_2$O (mw 457.02): C 63.08; H 7.72; N 9.19; Cl 7.76. Found C 62.95; H 7.37; N 8.92; Cl 7.79. [α]$_D$ = +29.7°. NMR: the diastereomeric mixture shows two signals for the alanyl methyl group ($f$ 0.88,d,J=7Hz and $f$ 1.16,d,J=7Hz), the methoxy function ($f$ 3.61s; $f$ 3.68s), and the 3,5 protons on the tyrosyl ring ($f$ 6.50s; $f$ 6.55s).

EXAMPLE 3

0,2,6-trimethyltyrosyl-N-(3-phenylpropyl)-D-alaninamide

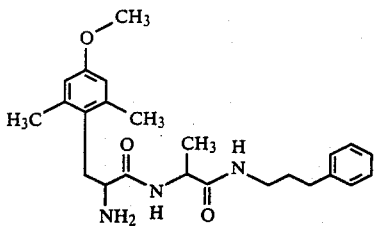

800 mg of the product of

EXAMPLE 2 was subjected to column chromatography on a Whatman Partisil 20 column, using CHCl$_3$: Ethanol 2B: NH$_4$OH (conc) as eluent. The first fractions that eluted were saved for further chromatography, as explained below. Later fractions contained pure material which was stripped to dryness, giving, after vacuum desiccator drying for 16 hr, the free base ¼ hydrate: Calc. for C$_{24}$H$_{33}$N$_3$O$_3$.¼ H$_2$O (mw 416.05) C 69.29; H 8.12; N 10.10. Found, C 69.30; H 8.45; N 9.97. [α]$_D$=−37.8° NMR: alanyl methyl group ∫ 1.21 d,5=7 Hz; methoxy ∫ 3.66s; 3,5-diH on tyrosine: ∫ 6.53s.

EXAMPLE 4

0,2,6-trimethyltyrosyl-N-(3-phenylpropyl)-D-alaninamide

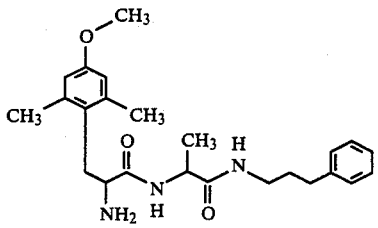

The early fractions from the preparation of the product of Example 3 (vide supra) were dried and applied to a Merck silica column using eluents of CHCl$_3$: Ethanol: NH$_4$OH conc. The first-emerging isomer was concentrated to dryness to give the free base ¼ hydrate: Calc. for C$_{24}$H$_{33}$N$_3$O$_3$ ¼H$_2$O (m.w. 416.04) C 69.29; H 8.12; N 10.10. Found C 69.42; H 8.31; N 9.88. [α]$_D$=+76.2° NMR: alanyl methyl signal at ∫ 1.06,d,J=7 Hz; methoxy at ∫ 3.66s; 3,5-diH of tyrosine at ∫ 6.54s.

EXAMPLE 5

0-ethyl−2,6-dimethyl-DL-tyrosyl-N-(3-phenylpropyl)-D-alaninamide, acetate (salt), hydrochloride (4:3:5;

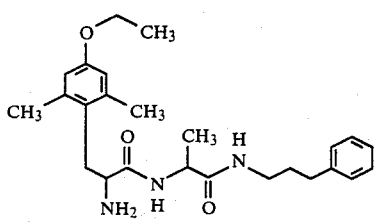

Boc−2,6-dimethyltyrosine (1.5 g, 4.85 mmol) was treated with ethyl iodide (3.78 g, 24.24 mmol) and potassium carbonate (2.68 g, 19 39 mmol) as described in Example 1. The hydrolysis of the resulting ester was run as described in Example 1.

The mixed anhydride synthesis of Boc-protected title compound was run as described in Example 2. The resulting BOC-dipeptide amide was purified by column chromatography on woelm silica, using mixtures of 1,1,1-trichloro−2,2,2-trifluoroethane and isopropanol.

The purified diastereomeric mixture was treated with HCl-dioxane in glacial acetic acid as described in Example 2. The reaction mixture was stripped to a solid, dissolved in aqueous methanol, filtered through celite, and partially reduced in volume to remove some methanol. The resulting solution was lyophilized to give the title compound as an acetic acid-water solvate: C$_{25}$H$_{35}$N$_3$O$_3$.1¼HCl.¾CH$_3$CO$_2$H.⅓H$_2$O (mw 518.44).

Calc C 61.39; H 7.68; N 8.11; Cl 8.55. Found C 61.09; H 7.28, N 8.28; Cl 8.54.

[α]=$_D$ −11.8° .NMR: Alanyl methyl signals at ∫ 0.85d,J=7 Hz and ∫ 1.14 d,5=7 Hz; 3,5-diH of tyrosine ∫ 6.45A, ∫ 6.53A; ethoxy function —OCH$_2$—∫3.85q,J=7H$_3$; —CH$_3$∫1.25 t,J=7H$_3$

EXAMPLE 6

2,6,dimethyl−0-(1-methylethyl)tyrosyl-N-(3-phenylpropyl)-D-alaninamide, hydrochloride (4:5)

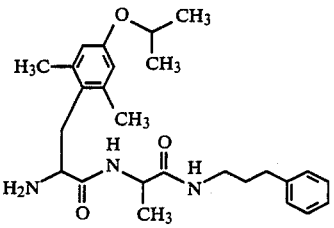

Boc-2,6dimethyltyrosione (1.5 g, 4.90 mmol) was reacted with isopropyl iodide (4.16 g, 24.5 mmol) in the presence of potassium carbonate (2.70 g, 19.6 mmol) in DMF as described in Example 1. After 24 hr, another equal portion of isopropyl iodide, and 1.25 g K$_2$CO$_3$ were added. After a further 24 hr of reaction, the mixture was worked up as described in Example 1, and the mixture was subjected to column chromatography on Woelm silica, using ethyl acetate-hexane eluents. The NMR of the product displays restricted rotation of the phenolic isopropyl ether function (doublet of doublets at ∫ 0.98,J=7H$_3$, 6 protons). The ester isopropyl function signal (doublet,J=7Hz) at ∫1.09 shows free rotation. This material was used directly:

The bis-isopropyl ester-ether (1.3 g, 3.21 mmol) was treated with NaOH (1.03 g, 25.7 mmol) as described in Example 1 to give the isopropyl ether free acid (1.0 g).

The isopropyl ether free acid was treated under mixed anhydride conditions as described in Example 2 to give the Boc-protected dipeptide amide (ether-acid 1.0 g, 2.75 mmol; N-methylmorpholine 0.32 ml, 2.89 mmol; isobutylchloroformate 0.37 ml, 2.84 mmol; (D)alanylphenylpropylamide 0.60 g, 2.89 mmol). In this case, the (D)alanylphenylpropylamide was used as the free base, not the HCl salt. Thus a second addition of N-methylmorpholine was not necessary. The product, 1.5 g, was subjected to column chromatography on porasil silica, using methanol-chloroform eluents. This purification separated the two diastereomers, giving a faster (iso-F) and a slower (iso-S) material. Each was used (separately) as in the next step:

The pure iso-F (494 mg.) was dissolved in glacial acetic acid (5 ml) and treated with dioxan-HCl (6.8N, 2 ml), and consequently worked up as described in Example 2. The product was isolated as $C_{26}H_{37}N_3O_3 \cdot 1\text{-}\frac{1}{8}$ HCl·$\frac{1}{2}H_2O$ mw 489.62

Calc C 63.78; H 8.05; N 8.58; Cl 8.15. Found C 63.60; H 7.95; N 8.35; Cl 7.93.

$[\alpha]_D = +104.2°$.

EXAMPLE 7

2,6,dimethyl-O-(1-methylethyl)tyrosyl-N-(3-phenylpropyl)-D-alaninamide, hydrochloride (8:11)

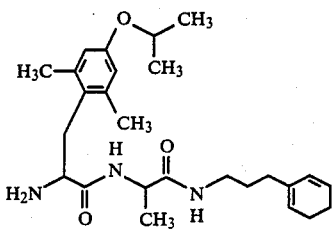

The pure iso-S (440 mg) from Example 6 was treated in the same manner as described in Example 6 to give $C_{26}H_{37}N_3O_3 \cdot 1\text{-}\frac{3}{8}HCl \cdot 1\text{-}\frac{1}{8}H_2O$ (mw 510.00)

Calc C 61.23; H 8.03; N 8.24; Cl 9.56. Found C 61.50; H 8.01; N 7.96; Cl 9.20.

$[\alpha]_D -73.3°$.

NMR: ipr methyls ∫ 1.19d,J=6 Hz; Alanyl methyl ∫ 1.15d,J=7 Hz.

EXAMPLE 8

N-[(1,1-dimethylethoxy)carbonyl]O-methyl-L-tyrosyl-N-(3-phenylpropyl)-D-alaninamide

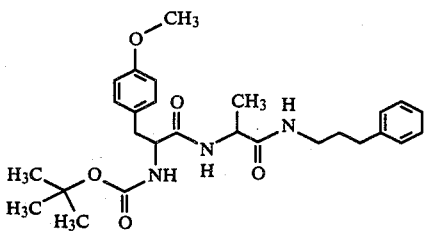

Boc-L-Tyrosine (commercially available, 10 g, 35.6 mmol) was treated with CH₃I (25.3 g, 177.9 mmol) and K₂CO₃ (19.7 g, 142.4 mmol) in DMF (150 ml) as described in Example 1. The product (9.68 g) shows NMR signals at ∫ 3.70s (phenolic methyl) and ∫ 3.60s (methyl ester), and aromatic proton signals at ∫ 6.80d,J=8 Hz and ∫ 7.11d,J=8 Hz.

O-Methyl-Boc-L-Tyrosine methyl ester (9.68 g, 35.6 mmol) was treated with NaOH (11.4 g, 284.8 mmol) as described in Example 1. The product shows NMR signals at ∫ 3.70s (phenolic methyl).

The free acid (8.34 g, 30.4 mmol) was treated with N-methyl morpholined (3.08 G, 30.4 mmol), isobutyl N-methylmorpholine (3.08 g, 30.4 mmol), isobutyl chloroformate (4.15 g, 30.4 mmol), and D-alanylphenylpropylamide (free base, 6.28 g, 30.4 mmol) as described in Example 2.

The resulting oil crystallized, giving the title compound as a mixture of diastereomers.

$C_{27}H_{37}N_3O_5$ (mw 483.61) $[\alpha]_D = +63.1°$.

Calc C 67.06; H 7.71; 8.69. Found C 67.18; H 7.84; N 8.79.

NMR: Ome ∫ 3.69s; arom.protons on Tyr: ∫ 6.78d,J=8 Hz; ∫ 7.13d,J=8 Hz; Boc methyls ∫ 1.30 s, D-ala methyl ∫ 1.09d,J=7 Hz.

EXAMPLE 9

O-methyl-L-tyrosyl-N-(3-phenylpropyl)-D-alaninamide, monohydrochloride

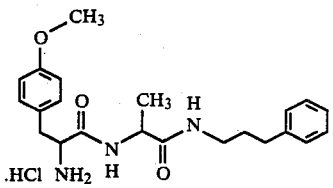

The compound from Example 8 (3 g. 6.21 mmol) was treated with glacial acetic acid (30 ml) and 6.8N HCl-dioxane (8 ml) as described in Example 2, to give the desired hydrochloride:

$C_{22}H_{29}N_3O_3 \cdot HCl$ (mw 419.95) $[\alpha]_D = +44.9°$.

Calc C 62.92; H 7.20; N 10.01; Cl 8.42. Found C 62.54; H 7.15; N 9.78; Cl 8.39.

NMR: OMe ∫ 3.71s; D-ala Me ∫ 1.05d,J=8 Hz.

EXAMPLE 10

N,O,2,6,-tetramethyl-D-tyrosyl-N-(3-phenylpropyl)-D-alaninamide, hydrochloride (4:5)

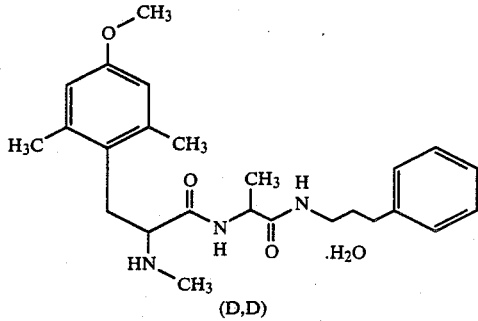

Boc—2,6-dimethyltyrosine (0.73 g, 2.36 mmol) was dissolved in DMF (20 ml) in a 100 ml round-bottomed flask. Pentane-washed NaH (9.43 mmol) was added. The flask was fitted with a drying tube and the mixture stirred. After 30 min, methyl iodide (2.34 g, 16.5 mmol) was added. The mixture was stirred for 4 hr. then more CH₃I (2.28 g, 16.1 mmol) was added. After a further 1.5 hr, another portion of NaH (3.33 mmol) was added, and the mixture was stirred overnight. The mixture was then partitioned between water and petroleum ether. The aqueous fraction was washed with fresh petroleum ether, the organic fractions were combined, dried (MgSO₄), filtered and stripped. The resulting oil was subjected to column chromatography on EMF silica using ethyl acetate-Skelly B eluents. This material was used directly:

O,N-dimethyl-2,6-dimethyltyrosine methyl ester (0.66 g, 1.88 mmol) was treated with NaOH (0.60 g, 15.0 mmol) as described in Example 1 to give the free acid (0.54 g). NMR: OMe signal at ∫ 3.66s; N-Me signal at ƒ2.59d; t.bu signal at ƒ1.28d. The N-Me and t-bu signals are doublets due to restricted rotation. Each signal colllapses to a singlet at elevated temperatures (70°).

O,N-dimethyl—2,6-dimethyltyrosine (0.54 g, 1.60 mmol) was treated with N-methylmorpholine (0.32 g, 3.20 mmol), isobutylchloroformate (0.22 g, 1.60 mmol), and (D)alanylphenylpropylamide hydrochloride as described in Example 2. The product, 0.82 g, was subjected to column chromatography on Whatman MAG 20 silica using ethyl acetate-hexane eluents. The two diastereomers were separated, giving a fast (iso-F), early-emerging isomer, and a slow (iso-S), late-emerging isomer.

The fast isomer (iso-F, 0.134 g), was treated with glacial acetic acid (10 ml) and 6.8N HCl in dioxane (2.5 ml) as described in Example 2. The resulting solid was dissolved in water, filtered through celite, and lyophilized to give the product.

$C_{25}H_{35}N_3O_3 \cdot 1\text{-}\frac{1}{4}HCl \cdot H_2O$ (mw 489.17).

Calc C 61.39; H 7.88; N 8.59; Cl 9.06 Found C 61.50; H 7.46; N 8.43; Cl 9.36.

$[\alpha]_D = -73.3°$.

NMR: OMe ƒ3.59s; N-Me ƒ3.04 m; D-Ala Methyl ƒ1.15d, J=7 Hz.

EXAMPLE 11

N,O,2,6,-tetramethyltyrosyl-N-(3-phenylpropyl)-D-alaninamide, monohydrochloride

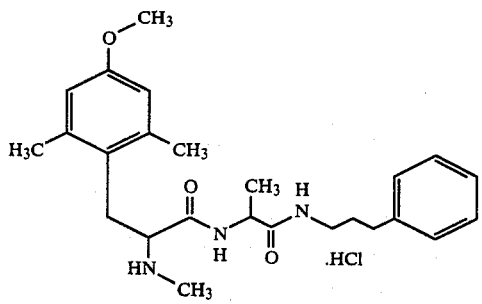

The slower isomer from Example 10 (iso-S, 0.18 g) was treated with glacial acetic acid (10 ml) and 6.8N HCl-dioxane (2.5 ml) as described in Example 2. The resulting solid was dissolved in aqueous methanol. The solution was reduced in volume and lyophilized. The resulting solid was dissolved/suspended in methylene chloride. A small amount of ether was added, and the mixture filtered. The filtrate was concentrated to a solid which was dried in a vacuum desiccator over molecular sieves overnight. The resulting product was the title $C_{25}H_{35}N_3O_3 \cdot HCl \cdot \frac{1}{2}H_2O$ (m.w. 471.04)

Calc C 63.75; H 7.92; N 8.92; Cl 7.53. Found C 63.85; H 7.73; N 8.81; Cl 7.71.

$[\alpha]_D = +94°$.

NMR: OMe ƒ;3.66s; NMe ƒ3.01d, J=6 Hz; D-ala Methyl ƒ0.89d, J=7 Hz.

EXAMPLE 12

N,2,6-trimethyl-0-(phenylmethyl)-DL-tyrosyl-N-(3-phenylpropyl)-D-alaninamide, monohydrochloride

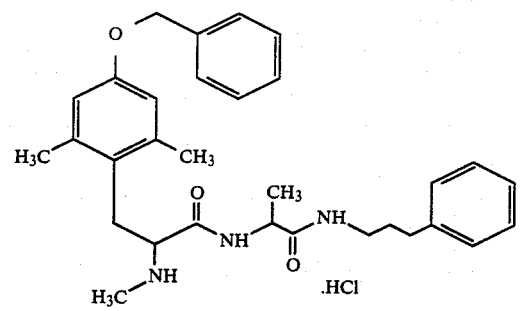

Boc—2,6-dimethyltyrosine (5.0 g, 16.2 mmol) was dissolved in DMF (100 ml), and $K_2CO_3$ (6.69 g, 48.5 mmol) was added. The mixture was stirred under a drying tube in a 250 ml round bottom single-necked flask. Benzyl bromide (11.1 g, 64.6 mmol) was added and the mixture stirred 24 hr. Then another portion of benzyl bromide (5.46 g, 31.9 mmol) and of $K_2CO_3$ (3.4 g, 24.6 mmol) was added and stirring was continued another 24 hr. The mixture was then partitioned between water and ether. The aqueous phase was washed with ether. The organic fractions were combined, dried (MgSO₄), filtered, and stripped to an oil. The oil was shaken with petroleum ether. This mixture was seeded, and product crystallized rapidly. NMR: benzyl protons (4 protons) ƒ4.99s. Total aromatic integration 12 protons.

O-benzyl-Boc-2,6-dimethyltyrosine benzyl ester (1.73 g, 3.53 mmol) was treated with sodium hydride (7.06 mmol, rinsed with petroleum ether) in DMF (22 ml) in a 100 ml pear-shaped flask, protected with a drying tube. After 15 minutes, CH₃I (2.51 g, 17.7 mmol) was added. After 2.5 hr, the reaction mixture was diluted to 150 ml with 0.5N KHSO₄, and the mixture was extracted thrice with ether. The organic fractions were combined, dried (MgSO₄), filtered and stripped to an oil (2.27 g). The oil was subjected to column chromatography on woelm silica, with ethyl acetate - methylene chloride eluents. The isolated product was O-benzyl-N-methyl-Boc-2,6-dimethyl tyrosine methyl ester:

NMR: CO₂Me ƒ3.65s, OCH₂φ ƒ5.03 (2 protons), ƒ7.35 (5.7 protons), N-Me ƒ2.55s, Boc-methyl asym. doublet ƒ1.30.

This ester (0.85 g, 2.06 mmol) was hydrolyzed with NaOH (0.66 g, 16.5 mmol) as described in Example 1. Product NMR: OCH₂φ ƒ5.01, ƒ7.35; N-Me ƒ2.59s; BOC-methyls-asym doublet ƒ1.27.

O-Benzyl-N-methyl-Boc-2,6-dimethyltyrosine (0.70 g, 1.69 mmol) was treated with N-methyl morpholine (0.18 g, 1.78 mmol), isobutylchloroformate (0.24 g, 1.75 mmol), and D-alanylphenylpropylamide (free base, 0.367 g, 1.78 mmol) as described in Example 2. The resulting oil was subjected to column chromatography on Merck silica, using ethyl acetate-methylene chloride eluents. The resulting material was further purified on a 4 mm chromatotron plate (centrifugal thick layer chromatography), using Hexane-ethyl acetate eluents. The resulting mixture of diastereomers (0.45 g) was subjected to hydrogenetion in tetrahydrofuran (30 ml) in the presence of palladium black (0.045 g) under 60 psi of hydrogen at 25° for 22 hr.- Then another portion of palladium black (0.045 g) was added, and the same conditions were reapplied for 65 hr. The resulting mixture was filtered, stripped to a solid, and subjected to column chromatography on woelm silica with eluents of ethanol: CH2Cl2 The first emerging compound was unchanged O-Benzyl-N-methyl-BOC-2,6-dimethyl (DL) tyrosyl-(D)alanylphenylpropylamide. This was saved for deblocking. The next compound was the expected O-deprotected product: N-methyl-Boc-2,6-dimethyl (DL) tyrosyl-(D)alanylphenylproplamide. This mixture of diastereomers was subjected to another column chromatography on Woelm silica, using a gradient elution of ethanol CH2Cl2 2.5:97.5 - 5.5:94.5. The first emerging compound (iso-F) and the second emerging compound (iso-S) were separately deblocked as in Examples 13 and 14.

O-Benzyl-N-methyl-BOC-2,6-dimethyl (DL)-tyrosyl-(D)-alanylphenylpropylamide was treated with methanol (1.5 ml) and 6.8N HCl in dioxane (1 ml) for 24 hr. The mixture was evaporated in a stream of nitrogen, and dissolved in aqueous methanol. The solution was filtered through Whatman 50 filter paper, reduced in volume in a nitrogen stream, and lyophilized. The product is $C_{31}H_{39}N_3O_3.HCl.\frac{3}{4}H_2O$ mw 551.64.

Calc C 67.50; H 7.58; N 7.62; Cl 6.43. Found C 67.44; H 7.41; N 7.47; Cl 6.69.

$[\alpha]_D= +51.8°$.

NMR: Benzyl methylene $\int 4.95s$, $\int 5.03s$, alanyl methyl $\int 1.16d, J=7$ Hz; $\int 0.88d, J=7$ Hz.

In a separate procedure, O-benzyl-N-methyl-BOC-2,6-dimethyl (DL) tyrosyl-(D)alanylphenylpropylamide was separated into its component diastereomers by column chromatography. Each diastereomer was treated with HCl in methanol-dioxane as described for the mixture of diastereomers. The products (separately) are the corresponding O-benzyl-N-methyl-2, 6-dimethyl-tyrosyl-(D) alanylphenylpropylamides: (D,D) C3, H39N3O3.HCl mw 538.13.

Calc: C 69.19; H 7.49; N 7.81; Cl 6.59. Found: C 69.50; H 7.52; N 7.92; Cl 6.66.

nmr: alanyl methyl $\int 1.18d$, J=7 Hz. n-methyl $\int 2.51$. Benzyl methylene $\int 4.95$.

$[\alpha]_D -62.3°$.

(L,D) $C_{31}H_{39}N_3O_3.HCl$ mw 538.13.

Calc: as for (D,D). Found: C 69.07; H 7.58; N 7.90; Cl 6.78.

NMR: alanyl methyl $\int 0.86d$, J=7 Hz. N-methyl $\int 2.50$. Benzyl methylene $\int 5.03$.

$[\alpha]D +95.5°$.

EXAMPLE 13

N,2,6-trimethyltyrosyl-N-(3-phenylpropyl)-D-alaninamide, monohydrochloride

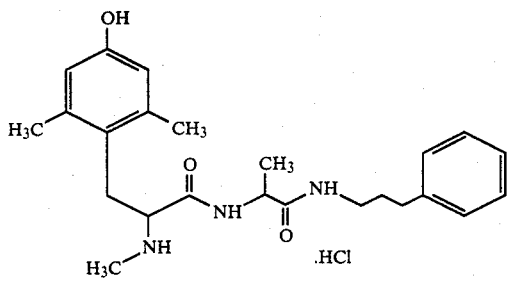

N-methyl-BOC-2,6-dimethyltyrosyl-(D)-alanyl-phenylpropylamide (iso F) from Example 12 was treated with methanol-HCl/dioxane as described in Example 12, except that no methanol was used after the removal of methanol-HCl/dioxane, so no reduction of volume was necessary before lyophilization. The product is $C_{24}H_{33}N_3O_3.HCl.1-\frac{1}{4}H_2O$ (mw 470.53).

Calc C 61.26; H 7.82; N 8.93. Found C 61.11; H 7.46; N 8.87.

$[\alpha]_D= -51.0°$.

NMR: Alanyl methyl $\int 1.18d$, J=7 Hz.

EXAMPLE 14

N,2,6-trimethyltyrosyl-N-(3-phenylpropyl)-D-alaninamide, hydrochloride (4:5)

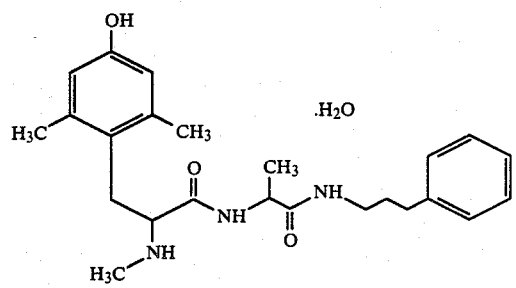

N-methyl-Boc-2,6-dimethyltrosyl-(D)-alanylphenylpropylamide (iso S) from Example 12 was treated with methanol-HCl/dixoane as described in Example 12. The product is $C_{24}H_{33}N_3O_3.1\frac{1}{2}HCl$. H2O mw 470.58

Calc C 61.26; H 7.74; N 8.93; Cl 8.46. Found C 61.23; H 7.40; N 8.88; Cl 8.83. $[\alpha]_D= +112°$.

NMR: (D)alanyl methyl $\int 0.90d, J=7H_Z$.

EXAMPLE 15

2,6-dimethyl-DL-tyrosyl-Nα-methyl-N-(3-phenylpropyl)-D-alaninamide, monohydrochloride

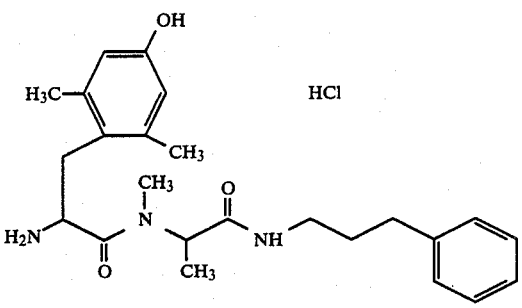

Carbobenzoxy (Z)-(D)alanine (22.3 g, 100 mmol) was dissolved in THF (300 ml). Methyl iodide (114 g, 800 mmol) was added, and the mixture cooled to −5°. Sodium hydride (300mmol, 50% suspension in mineral oil) was added over a 1 hr period. The temperature was maintained at +10° for another hour. Another 300 ml of THF was added, and the mixture was stirred at room temperature 68 hr. Ethyl acetate (500 ml) was added to the reaction mixture, followed by H2O (10 ml). This mixture was concentrated and then partitioned between water and ether. The aqueous layer was washed twice with ether, the organic fractions were combined and rinsed with saturated aqueous NaHCO3. The aqueous fractions were combined. The organic layers were then discarded, and the aqueous fraction was acidified with citric acid solution to pH4. The acidified aqueous fraction was extracted with ethyl acetate. The organic fraction was washed twice with 5% Na₂S₂O₃ solution and once with water. The organic fraction was dried (MgSO₄), filtered, and stripped to an oil (22.2 g). Crystallization was effected with ethyl acetate-Skelly B mixtures. NMR (CDCl₃): N-Me ∫2.89s, alanylmethyl ∫1.43. [α]$_D$ (Ethanol)=24.5°.

N-Methyl-Z-(D)alanine (7.12 g, 30.0 mmol) was treated with N-methyl morpholine (3.04 g, 30.0 mmol), isobutylchloroformate (4.10 g, 30.0 mmol), and 3-phenylpropylamine (4.06 g, 30.0 mmol), as described in Example 2, giving 9.87 g of a light yellow oil. This oil was subjected to hydrogenation (60 psi H₂) in methanol at 25° with a 10% Pd/C catalyst to give the deprotected N-methyl-(D)-alanyl-phenyproplyamide as an oil (5.85 g) after filtration and concentration.

N-Methyl-(D)-alanylphenylpropylamide (2.88 g, 13.05 mmol) replaced (D)alanylphenylpropylamide in the mixed anhydride synthesis described in Example 2. It was reacted with the intermediate formed by the reaction of Boc-2,6-dimethyltyrosine (4.00 g, 13.05 mmol) with isobutylchloroformate (3.58 g, 26.1 mmol—notice that two moles of isobutylchloroformate are used —the second mole acts as a protecting group for the free phenol) in the presence of N-methylmorpholine (2.64 g, 26.1 mmol) in methylene chloride. The final amide synthesis from the mixed anhydride was run overnight at 25°. After the workup described in Example 2 the material was used as is, without chromatography.

O-Isobutoxycarbonyl-Boc-2,6-(D,L)-dimethyl tyrosyl-N-methyl-(D)alanylphenylpropylamide (6.71 g) was dissolved in methanol (100 ml) and stirred with K₂CO₃ (1.98 g) for 4 hr. The mixture was concentrated and partitioned between CH₂Cl₂ and 0.5N KHSO₄. The organic layer was extracted twice with 0.5N KHSO₄. Each aqueous wash was back-washed with fresh CH₂Cl₂. The organic fractions were combined, washed thrice with saturated NaHCO₃ (backwash e.g. with CH₂Cl₂), washed with saturated brine, dried (Na₂SO₄ followed by CaSO₄), filtered, and stripped to an oil (5.50 g). The oil was subjected to column chromatography on porasil silica, using ethyl acetate-methylene chloride eluents, thus isolating the mixture of disasteromers (3.47 g). This oil was triturated with Skelly B-Ether mixtures to give 3.18 g of a foam.

This foam (3.03 g) was treated with glacial acetic acid (24 ml) and 6.2N HCl/dioxane (9.6 ml) as described in Example 2, to give the desired 2,6-dimethyl(D,L) tyrosyl-N-methyl-(D)-alanylphenylpropylamide hydrochloride.

$C_{24}H_{33}N_3O_3$·HCl·¼H₂O mw 452.51.

Calc C 63.70; H 7.69; N 9.29; Cl 7.83. Found C 63.45; H 7.60; N 9.10; Cl 7.70.

[α]$_D$=+36.3° NMR: N-methyl-partially hidden under DMSO, ∫2.58; alanyl methyl-∫0.97d,J=7 Hz; ∫1.15d,J=7 Hz.

EXAMPLE 16

2,6-dimethyl-DL-tyrosyl-N-methyl-N-(3-phenylpropyl)-D-alaninamide, monohydrochloride

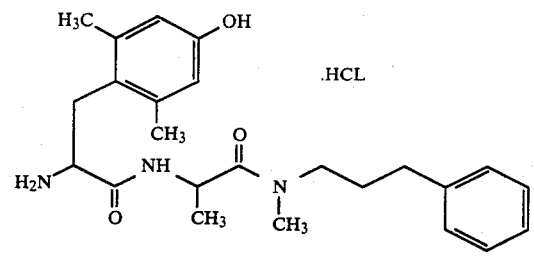

Z-(D)-alanine (10.0 g, 44.8 mmol) was treated with N-methyl morpholine (4.54 g, 44.8 mmol), isobutylchloroformate (6.12 g, 44.8 mmol), and N-methyl-3-phenylpropylamine (6.69 g, 44.8 mmol) in methylene chloride as described in Example 2, giving an oil (14.5 g).

A portion (4.07 g) of this oil was subjected to repeated hydrogenation (60 psi H₂) in THF with a 5% Pd/C catalyst to give the deprotected (D)alanyl-N-methyl-3-phenylpropylamide (2.50 g).

Boc-2,6-dimethyltyrosine (3.54 g, 11.5 mmol) and. N-methylmorpholine (1.16 g, 11.5 mmol) were combined in a mixture of DMF (13 ml) and methylene chloride (13 ml). The reaction was protected by N₂, stirred 30 min, and then cooled to −50°. Isobutylchloroformate (1.56 g, 11.5 mmol) was then added, and the temperature was permitted to rise to −10°. The reaction mixture was then recooled to −50°, and (D)alanyl-N-methyl-3-phenylproplyamide (2.50 g in a small amount of CH₂Cl₂) was added. The mixture was warmed to room temperature, and stirred for 3 hr. The reaction was worked up as described in Example 2, giving 5.10 g of foam. This foam was suspended to CH₂Cl₂, filtered, and stripped to an oil (4.0 g). This oil was subjected to column chromatography on porasil silica, using methanol-chloroform eluents. The product was the mixture of Boc-protected diastereomers (2.40 g).

A portion of this mixture (0.50 g) was treated with dioxane (20 ml) and 6.8N HCl/dioxane (2.88 ml) for 20 hr. at 25°. The mixture was stripped to a foam, triturated thrice with ether, and dried in an abderhalden apparatus at 78° at 0.01 torr for 2 hr. The product was the desired hydrochloride hemihydrate:

$C_{24}H_{33}N_3O_3$·HCL·½H₂O mw 457.02

Calc C 63.08; H7.72; N 9.19; Cl 7.76. Found C 63.07; H7.47; N 8.96; Cl 8.16.

[α]$_D$= +21.2°. NMR N-methyl: ∫2.79t, collapses to ∫2.82d at 60°; alanyl methyl ∫1.12m, ∫0.81m; these collapse to doublets at 60°. These are probably caused by restricted rotations due to interactions of the alanyl and phenylpropylamide methyl functions.

EXAMPLE 17

2,6-dichloro-4-chloromethylanisole.

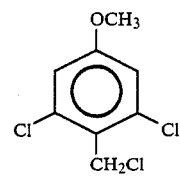

53.8 g (333 mmol) of dichloro anisole, 340 ml conc HCl, and 52.5 ml 37% formaldehyde (1.72 mol) were heated at 50° overnight. The reaction was diluted with H$_2$O and saturated brine, and extracted twice with ether. The ether phases were combined, washed with water, satureted NaHCO$_3$, saturated brine, dried with MgSO$_4$ and concentrated to a syrup (56 g). Chromatography on Waters 500 with two normal phase silica cartridges eluting with hexane at 250 ml/Min. obtained 28 g white solid. Calcd. C 42.61 H39.61 Cl 47.17 Found C 39.61 H2.79 Cl 50.34. C$_8$H$_7$OCl$_3$ (mw 225.50).

EXAMPLE 18 diethyl (acetylamino)[(2,6-dichloro-4-methoxyphenyl)methyl]-propanedioate

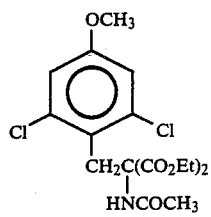

Under Ar, 3.4 g (137 mmol) Na was dissolved in absolute EtOH, followed by addition of 32.3 g (147 mmol) diethyl acetamidomalonate and 1 hr. reflux. Then 27.9 g (124 mmol) of the product of Example 17 was added and refluxed overnight. The reaction was stripped and mixed with 400 ml 1:1 CHCl$_3$/H$_2$O, the organic phase was extracted with H$_2$O and then Sat'd NaCl, dried with MgSO$_4$ and concentrated to a solid (43 g). The solid was chromatographed on Waters 500 with two normal phase silica columns, eluting with 25% ethyl acetate/toluene at 250 ml/min., giving 26.7 g of solid, m.p. 153.5°–156.4°.

Calcd. C 50.26; H 5.21; N 3.45; Cl 17.45. Found: C 50.33; H 5.12; N 3.38; Cl 17.79. C$_{17}$H$_{21}$NO$_6$Cl$_2$ (mw 406.27).

EXAMPLE 19

2,6-dichloro-DL-tyrosine, monohydrochloride

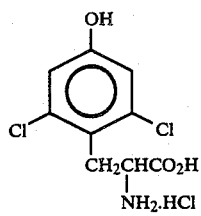

23 g (56.6 mmol) of the malonate adduct (Example 18), 50 g (362 mmol) K$_2$CO$_3$ and 45 g (285 mmol) phenyl selenol were refluxed in 200 ml DMF under N$_2$ overnight. The reaction was diluted with 1L H$_2$O, extracted with ether; the aqueous phase was acidified with HCl and extracted with Sat'd NaCl solution, dried with MgSO$_4$ and concentrated to an oil (37 g). The oil was shaken with 150 ml Skelly B and the supernatant decanted 3X before crystallization of the oil with 100 ml CH$_2$Cl$_2$, giving 11.5 g of the N-acetyl amino acid as a solid. This compound was then refluxed in 160 ml 6N HCl overnight, cooled and filtered to give 9.9 g crystals.

Calcd: C 37.72; H 3.53; N 4.89; Cl 37.12. Found: C 37.63; H 3.45; N 4.83; Cl 36.20. C$_9$H$_{10}$NO$_3$Cl$_3$ (mw 286.55).

EXAMPLE 20

N-[(1,1-dimethylethoxy)carbonyl]-2,6-dichloro-DL-tyrosine

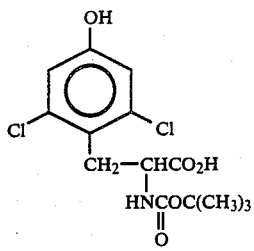

9.9 g (4.00 mmol) of the product of Example 19 was dissolved in 25 ml H$_2$O and the pH adjusted to 9.5 with 10% NaOH, giving a final vol. of 100 ml. t-BuOH(100 ml) and 14.5 g (64 mmol) (Boc$_2$)O were added and the pH was maintained at 9.5 with 10% NaOH. The pH was raised to 13 and the reaction was warmed to 50° to saponify O(Boc)$_2$. The reaction mixture was cooled, acidified to pH2 with 1M KHSO$_4$ and extracted with ethyl acetate. The organic phase was extracted with saturated brine, dried with MgSO$_4$ and concentrated. The residue was crystallized with CH$_2$Cl$_2$ to give 8.5 g crystals.

Calcd: C; 48.02; H 4.89; N 4.00; Cl 20.25. Found C 47.36; H 4.64; N 3.75; Cl 20.53. C$_{14}$H$_{17}$NO$_5$Cl$_2$ (mw 350.19).

EXAMPLE 21

N-[(1,1-dimethylethoxy)carbonyl]-2,6-dichloro-DL-tyrosyl-N-(3-phenylpropyl)-D-alaninamide

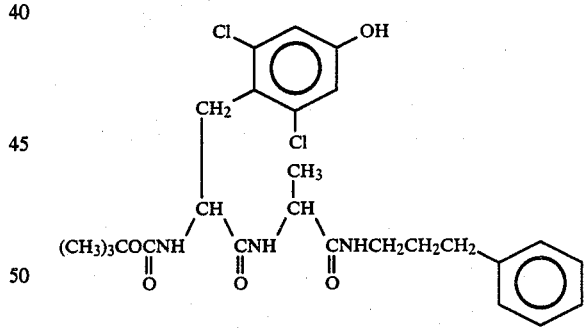

7 g (20.0 mmol) of the product of Example 20 was dissolved in 60 ml CH$_2$Cl$_2$ containing 2.02 g (20.0 mmol) N-Me Morpholine under N$_2$, cooled to −30° C., and 2.73 g (20.00 mmol) isobutyl chloroformate was added. After 15 minutes 5 g (24 mmol) D-alanylphenyl-propylamide was added after raising the temperature to −20° C. The reaction was stirred at room temperature overnight. The reaction was diluted with 500 ml EtOAc, and extracted with 1M KHSO$_4$, Sat'd NaHCO$_3$, Sat'd NaCl and dried with MgSO$_4$. Concentrating the solution gave 10 g of foam. Chromatography on waters 500 with two normal phase silica columns eluting with 1.6% methanol/CHCl$_3$ at 250 ml/min. gave 1.3 g of a fast moving isomer A and 1.1 g of a slow moving isomer B. C$_{26}$H$_{33}$N$_3$O$_5$Cl$_2$ (mw 538.47).

Isomer A. Calcd. C 58.00, H 6.18, N 7.80, Cl 13.17. Found: C 57.82, H 6.13, N 7.68, Cl 13.21.

$[\alpha]_D = -1.9°$.

Isomer B. Calcd. C 58.00, H 6.18, N 7.80, Cl 13.17. Found C 57.87, H 6.06, N 7.62, Cl 13.25.

$[\alpha]_D = +6.6°$.

EXAMPLE 22

2,6,dichlorotyrosyl-N-(3-phenylpropyl)-D-alaninamide, monohydrochloride

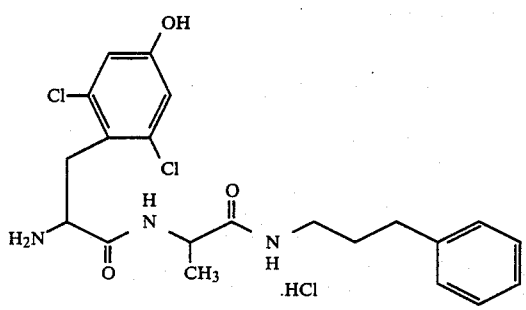

1.3 g (2.40 mmol) of Isomer A from Example 21 was dissolved in 8 ml glacial acetic acid and 8 ml 6∫HCl-/Dioxane. After this, the solution was concentrated to a small volume and added to ether and filtered. 0.90 g. $C_{21}H_{26}Cl_3N_3O_3 \cdot \frac{1}{2}H_2O$ (mw 483.82)

Calcd: C 52.13; H 5.64; N 8.69; Cl 21.98. Found: C 51.94; H 5.33; N 8.62; Cl 21.63.

$[\delta]_D = -57°$.

NMR Ala methyl ∫=1.18d, J=6 Hz Tyr (ph-H)δ=6.80.

EXAMPLE 23

2,6,dichlorotyrosyl-N-(3-phenylpropyl)-D-alaninamide, monohydrochloride

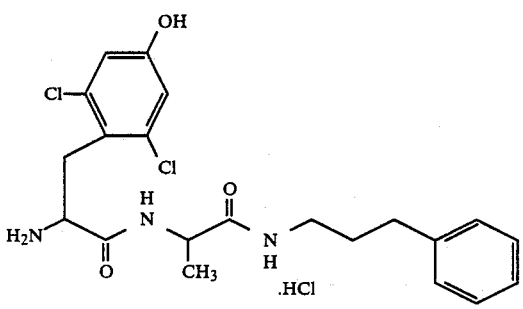

Isomer B from Example 21 was treated in the same manner as described for Isomer A in Example 22, giving the title compound. $C_{21}H_{26}Cl_3N_3O_3 \cdot \frac{1}{2}H_2O$ Calcd (as in Example 22). Found: C 52.03; H 5.58; N 8.40; Cl 21.17.

$[\alpha]_D = +53.6°$.

NMR Ala (CH₃) ∫1.00 d (J=6 Hz) Tyr (Ph H)δ=6.85.

EXAMPLE 24

2,4,6-trimethyl-L-phenylalanyl-N-(3-phenylpropyl)-D-alaninamide, monohydrochloride

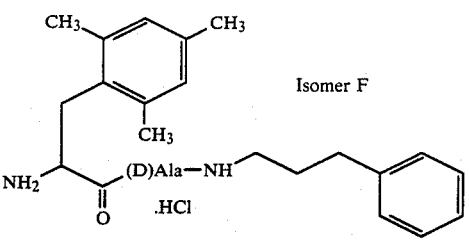

2,4,6-Trimethylbenzyl chloride (200 g, 1.19 mol) was treated with the sodium salt of diethyl acetamidomalonate (274 g, 1.31 mol malonate; 30.1 g, 1.31 mol sodium) as described in Example 18 giving 253 g of 2,4,6-trimethyl-N-acetyl-α-carboxyethyl-phenylalanine.

This substance (241 g) was dissolved in 1 l of refluxing conc HCl. Refluxing continued 18 hr. Water (1 l) was then added, and reflux was resumed for a short time. The reaction mixture was allowed to cool. The product crystallized out, was collected by filtration, and washed sequentially with cold 1N HCl, acetone, and ether. Recrystallization from water gave 68 g of 2,4,6-trimethylphenylalanine.

2,4,6-trimethylphenlalanine (62 g, 254 mmol) was treated with di-t-butyldicarbonate (58 g, 267 mmol) as described in Example 20, giving 64 g of Boc-2,4,6-trimethylphenylalanine.

Boc-2,4,6-trimethylphenylalanine (7.87 g, 25.6 mmol) was treated with N-methylmorpholine (2.58 g, 25.6 mmol), isobutylchloroformate (3.55 g, 25.6 mmol), and (D)alanylphenylpropylamide (free base, 6.0 g, 25.6 mmol) as described in Example 2. The product mixture was subjected to column chromatography in porasil silica, using ethanol-methylene chloride eluents. The two diasteromers were thus separated.

The isomer emerging first from the column (2.23 g) was treated with glacial acetic acid (40 ml) and 6.8N HCl/dioxane (7.5 ml) as described in Example 2, giving the desired 2,4,6-trimethyl-(L)-Phenylalanyl-(D)alanylphenylpropylamide:

$C_{24}H_{33}N_3O_2 \cdot HCl$ (mw 432.02). $[\alpha]_D = +115.7°$.

Calc: C 66.72; H7.93; N 9.73. Found: C 66.25; H7.85; N 9.61.

NMR (CD₃OD): 4-methyl ∫2.22s; alanyl methyl ∫0.98d.

EXAMPLE 25

2,4,6-trimethylphenylalanyl-N-(3-phenylpropyl)-D-alaninamide, monohydrochloride

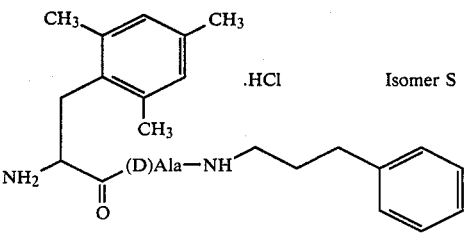

The isomer emerging last from the column chromatography (3.63 g) in Example 24 was treated with glacial acetic acid (50 ml) and 6.8N HCl/Dioxane (13 ml) as described in Example 24, to give the desired 2,4,6-trimethyl-(D)-Phenylalanyl-(D)-alanylphenylpropylamide:

$C_{24}H_{33}N_3O_2 \cdot \frac{1}{2}H_2O$ (mw 436.52). $[\alpha]_D = -74.7°$.

Calc: C 66.03; H7.97; N 9.63. Found: C 66.19; H7.96; N 9.61.

NMRA (CH$_3$OD): 4-methyl ∫2.12; alanyl methyl ∫1.27d. Example 26

N-[(1,1-dimethylethoxy)carbonyl]-2,6-dimethyl-O-(phenylmethyl)-DL-tyrosine

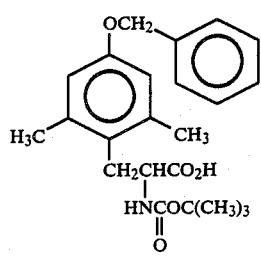

O-benzyl-Boc-2,6-dimethyltyrosine benzyl ester, prepared as in Example 12 (5 g, 10.21 mmol), was treated with NaOH(3.27 g, 81.70 mmol), as described in Example 1, giving the title compound. NMR: benzyl methylene at ∫4.99s (2 protons). EXAMPLE 27

2,6-dimethyl-O-(phenylmethyl)-L-tyrosyl-N-(3-phenyl-propyl)-D-alaninamide, monohydrochloride

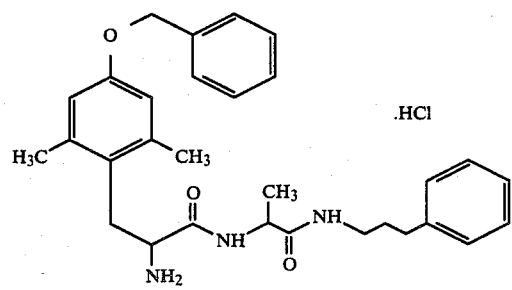

O-benzyl-Boc-2,6-dimethyltyrosine (3.50 g, 8.77 mmol) was treated with N-methylmorpholine (0.93 g, 9.21 mmol), isobutylchoroformate (1.23 g, 9.04 mmol), and D-alanylphenylpropylamide (1.90 g, 9.04 mmol) as described in Example 2. The resulting material was subjected to column chromatography on porasil silica, using mixtures of methanol-chloroform as eluents. Two products were isolated, a fast (iso-F) and a slow (iso-S) isomer.

The fast moving isomer (iso-F: first to emerge from column, 1 g) was treated with glacial acetic acid (10 ml) and 6.8N HCl in dioxane (3 ml) as described in Example 2. The resulting solid was dissolved in aqueous methanol, filtered, and lyophilized to give the title compound.

$C_{30}H_{37}N_3O_3 \cdot HCl \cdot \frac{3}{4}H_2O$ (mw 537.62).

Calcd: C 67.02; H7.41; N 7.82; Cl 6.59. Found: C 67.03; H7.12; N 8.21; Cl 6.84.

$[\alpha]_D = +115.7$.

NMR: benzyl methylene: ∫5.03s; alanyl methyl ∫0.83d, J=7 Hz.

EXAMPLE 28

2,6-dimethyl-O-(phenylmethyl)-D-tyrosyl-N-(3-phenyl-propyl)-D-alaninamide, hydrochloride

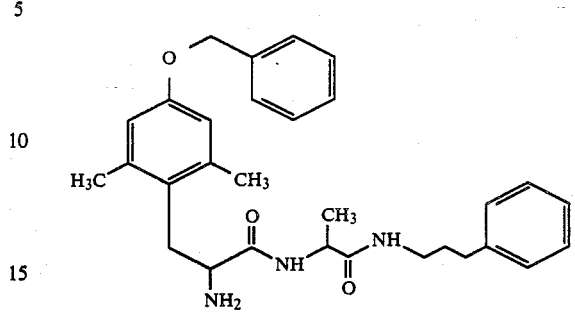

The slow moving isomer from Example 27 (iso-S, last to emerge from the column, 1 g) was treated and worked up as described for the iso-F compound in Example 27, giving the title compound $C_{30}H_{37}N_3O_3 \cdot 1\frac{1}{4}HCl \cdot \frac{1}{2}H_2O$ (mw 537.67).

Calcd: C 67.02; H7.33; N 7.82; Cl 7.42. Found: C 66.84; H7.14; N 7.98; Cl 7.15.

$[\alpha]_D = -69.7$.

NMR: benzyl methylene: ∫4.95s; alanyl methyl ∫1.14d, J=7 Hz.

EXAMPLE 29

N-[(1,1-dimethylethoxy)carbonyl]-2,6-dimethyl-DL-tyrosine, methyl ester

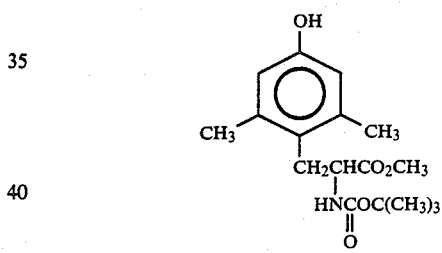

A 11-three-necked flask containing methanol (250 ml) and fitted with a thermometer, a dropping funnel, and a Y-tube with a N$_2$ inlet and a drying tube outlet was cooled to −70°. Thionyl chloride (38.74 g, 325 mmol) was added dropwise, keeping the reaction temperature at or below −60°. After the addition was complete, the mixture was warmed to 0°. 2,6-dimethyltyrosine hydrochloride (40 g, 162 mmol) was added and the mixture was stirred under N$_2$ at room temperature overnight. The reaction mixture was then filtered to remove traces of solid, and stripped to an oil, which was triturated with ether and allowed to stand. The oil solidified overnight, and was dried in a vacuum oven at 30°, giving the methylester. NMR: methoxy ∫3.45s, 3,5-diH on aromatic ring ∫6.44s.

This product (40 g, 154 mmol) was suspended in CHCl$_3$ (800 ml). N-methylmorpholine (15.5 g, 16.94 ml, 154 mmol) was added, and the mixture stirred under nitrogen for 40 min. Di-t-butyldicarbonate (33.61 g, 35.42 ml, 154 mmol) was added, and the mixture was stirred overnight. The mixture was washed twice with water, dried (MgSO$_4$), filtered, and stripped. The residue was triturated and filtered with hexane, giving the title compound. NMR: methoxy ∫3.50s, Boc-methyls ∫1.35s.

EXAMPLE 30

O-[(4-cyanophenyl)methyl]-N-[(1,1-dimethylethoxy)-carbonyl]-2,6-dimethyl-DL-tyrosine

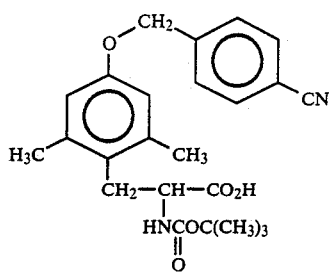

A dispersion of NaH in oil (27.3 mmol) was weighed into a 1 l round bottom flask containing a magnetic stirrer. The dispersion was washed with hexane to remove the mineral oil, and the flask was immediately charged with tetrahydrofuran (THF) (200 ml). Boc-2,6-dimethyltyrosine methylester (Example 29, 8 g, 24.8 mmol) was added and a drying tube was inserted. The mixture was stirred for 2 hr. α-Bromo-p-toluonitrile (5.24 g, 26.8 mmol) was then added, and the mixture stirred at room temperature overnight. A thin layer chromotogram (2:1 Skelly B: Ethyl Acetate) was then run. If starting material was still present, NaH dispersion (½ molar amount) and alkylating agent (½ molar amount) were added and the reaction run another 24 hr at room temperature. The mixture was then poured into water (1.2 l) and rapidly extracted thrice with $CH_2Cl_2$. The organic fractions were combined, dried ($MgSO_4$), and stripped to give a product (O-(p-cyanobenzyl)-Boc-2,6-dimethyltyrosine methyl ester) which was directly hydrolyzed with NaOH as described in Example 1 to give the title compound. NMR: benzyl methylene ∫5.10 s; tyrosyl aromatic protons ∫6.60s; benzyl aromatic protons centered at ∫7.65.

EXAMPLE 31

O-[(4-chlorophenyl)methyl]-N-[(1,1-dimethylethoxy)-carbonyl]-2,6-dimethyl-DL-tyrosine

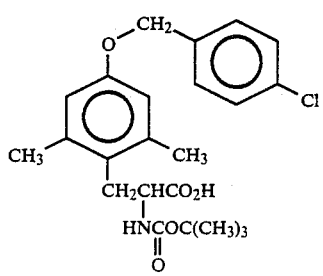

Replacement of α-bromo-p-toluonitrile in Example 30 with 4-chlorobenzyl chloride gave the title compound. NMR: benzyl methylene ∫5.00 s; tyrosyl aromatic protons ∫6.60s; benzyl aromatic protons all at ∫7.40s.

EXAMPLE 32

N-[(1,1-dimethylethoxy)carbonyl]-2,6-dimethyl-O-[(2-methylphenyl)methyl]-DL-tyrosine

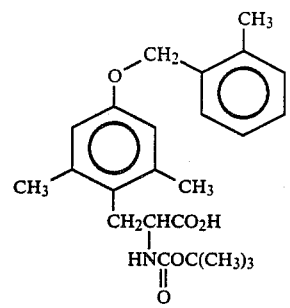

Replacement of α-bromo-p-toluonitrile in Example 30 with α-bromo-o-xylene gave the title compound. NMR: benzyl methylene ∫4.95s; tyrosyl methyl groups ∫2.25s; benzyl methyl group ∫2.30s.

EXAMPLE 33

N-[(1,1-dimethylethoxy)carbonyl]-2,6-dimethyl-O-[(4-nitrophenyl)methyl]-DL-tyrosine

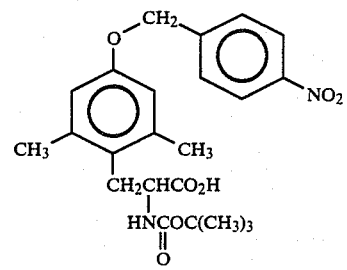

Replacement of α-bromotoluonitrile in Example 30 with p-nitrobenzylbromide gave the title compound. NMR: benzyl methylene ∫5.18s; tyrosyl aromatic protons ∫6.65s; benzyl protons ∫7.60d, J=8 Hz and ∫8.20d, J=8 Hz.

EXAMPLE 34

N-[(1,1-dimethylethoxy)carbonyl]-O-[(4-fluorophenyl)-methyl]-2,6-dimethyl-DL-tyrosine

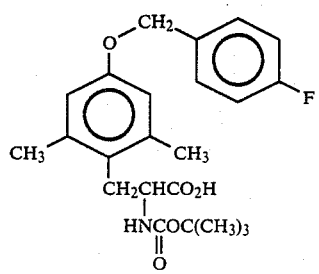

Replacement of α-bromotoluonitrile in Example 30 with 4-fluorobenzyl bromide gave the title compound. NMR: benzyl methylene ∫5.00 s; tyrosyl aromatic protons ∫6.60s; benzyl aromatic protons centered at ∫7.25.

EXAMPLE 35

N-[(1,1-dimethylethoxy)carbonyl]-2,6-dimethyl-O-[(4-methylphenyl)methyl]-DL-tyrosine

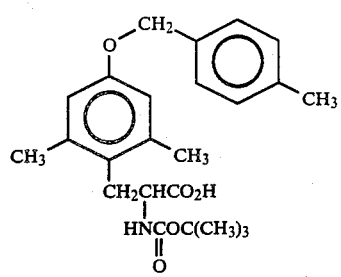

Replacement of α-bromotoluonitrile in Example 30 with α-bromo-p-xylene gives the title compound.

EXAMPLE 36

N-[(1,1-dimethylethoxy)carbonyl]-O-[[4-(1,1-dimethylethyl)phenyl]methyl]-2,6-dimethyl-DL-tyrosine

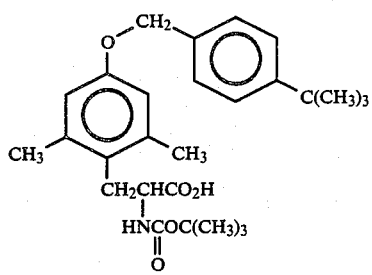

Replacement of α-bromotoluonitrile in Example 30 with p-t-butylbenzyl bromide gives the title compound.

EXAMPLE 37

O-[(4-chlorophenyl)methyl]-2,6-dimethyltyrosyl-N-(3-phenylpropyl)-D-alaninamide, monohydrochloride

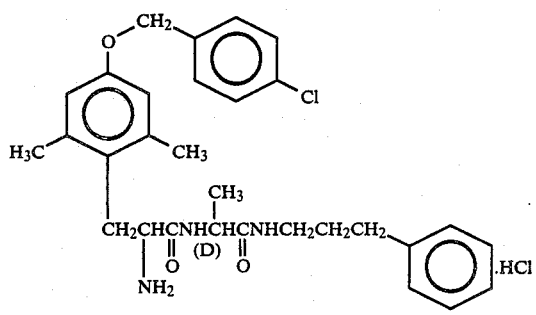

The product of Example 31, when exposed to the mixed anhydride condensation in Example 2, instead of O-methyl-Boc-2,6-dimethyltyrosine, gives after workup, a mixture of diasteremoers which is separated by column chromatography. Each diastereomer is then treated with dioxane/HCl/glacial acetic acid as described in Example 2, to give the two diastereomers of the title compound.

EXAMPLE 38

2,6-dimethyl-O-[(2-methylphenyl)methyl]-L-tyrosyl-N-(3-phenylpropyl)-D-alaninamide, monohydrochloride

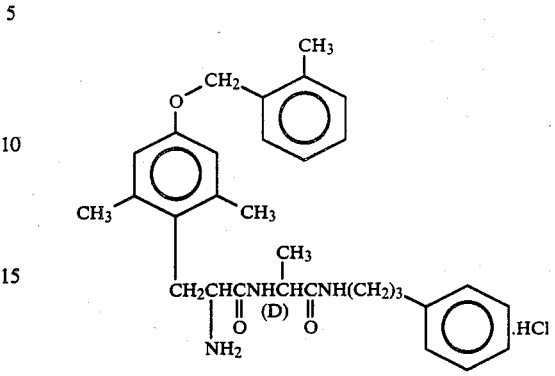

The product of Example 32, when exposed to the mixed anhydride condensation in Example 2, instead of O-Methyl-Boc-2,6-dimethyltyrosine, gave after workup, a mixture of diastereomers which was separated by column chromatography. Each diastereomer was then treated with dioxane/HCl/glacial acid as described in Example 2, to give the two diastereomers of the title compound: For the L,D diastereomer: $C_{31}H_{39}N_3O_3 \cdot HCl \cdot \tfrac{3}{4}H_2O$ (mn 551.64).

Calc: C 67.50; H 7.58; N 7.62; Cl 6.43. Found: C 67.62; H 7.27; N 7.81; Cl 6.62.

$[\alpha]_D = +108.4°$. NMR: Alanyl methyl signal at ∫0.85, d, J=8 Hz. O-Methyl signal on benzyl group: ∫2.24s.

EXAMPLE 39

2,6-dimethyl-O-[(4-nitrophenyl)methyl]tyrosyl-N-(3-phenylpropyl)-D-alaninamide, monohydrochloride

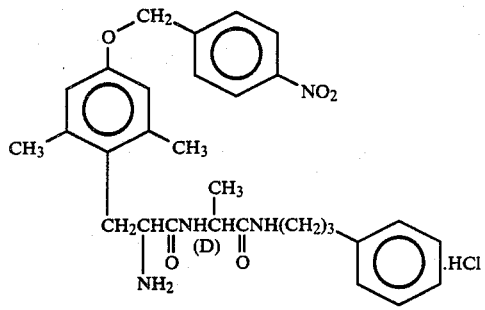

The product of Example 33, when exposed to the mixed anhydride condensation in Example 2, instead of O-Methyl-Boc-2,6-dimethyltyrosine, gave, after workup, a mixture of diastereomers which was separated by column chromatography. Each diasteromer was then treated with dioxane/HCl/glacial acetic acid as described in Example 2, to give the two diasteromers of the title compound having $[\alpha]_D$ of −27.9 (D,D) and +72.7° (L,D) in methanol.

(D,D): $C_{30}H_{36}N_4O_5 \cdot HCl \cdot 1\tfrac{1}{4}H_2O$ (mw 591.63).

Calc: C 60.90; H 6.52; N 9.47; Cl 5.99. Found: C 60.58; H 6.36; N 9.46; Cl 6.27.

NMR: alanyl methyl ∫1.28d.

(L,D) $C_{30}H_{36}N_4O_5 \cdot 1\tfrac{1}{4}HCl \cdot 1\tfrac{1}{2}H_2O$ (mw 605.25).

Calc: C 59.53; H 6.70; N 9.26; Cl 7.32. Found: C 59.13; H 6.36; N 9.05; Cl 7.27.

NMR: alanyl methyl ∫0.95d.

EXAMPLE 40

O-[(4-fluorophenyl)methyl]-2,6-dimethyltyrosyl-N-(3-phenylpropyl)-D-alaninamide, monohydrochloride.

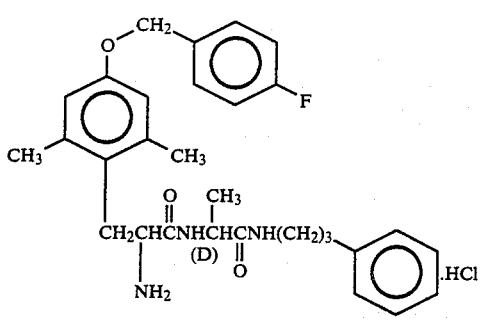

The product of Example 34, when exposed to the mixed anhydride condensation in Example 2, instead of O-Methyl-Boc-2,6-dimethyltyrosine, gave after workup, a mixture of diastereomers which was separated by column chromatography. Each diastereomer was then treated with dioxane/HCl/glacial acid as described in Example 2, to give the two diastereomers of the title compound having $[\alpha]_D$ of $-64.2°$ and $+94.0°$ in methanol.

EXAMPLE 41

2,6-dimethyl-O-[(4-methylphenyl)methyl]tyrosyl-N-(3-phenylpropyl)-D-alaninamide, monohydrochloride

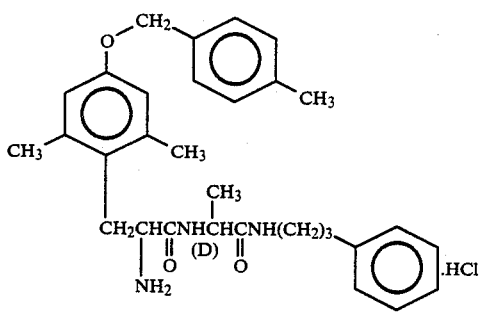

The product of Example 35, when exposed to the mixed anhydride condensation in Example 2, instead of O-Methyl-Boc-2,6-dimethyltyrosine, gives after Workup, a mixture of diastereomers which is separated by column chromatography. Each diastereomer is then treated with dioxane/HCl/glacial acid as described in Example 2, to give the two diastereomers of the title compound.

EXAMPLE 42

O-[[4-(1,1-dimethylethyl)phenyl]methyl]-2,6-dimethyltyrosyl-N-(3-phenylpropyl)-D-alaninamide, monohydrochloride

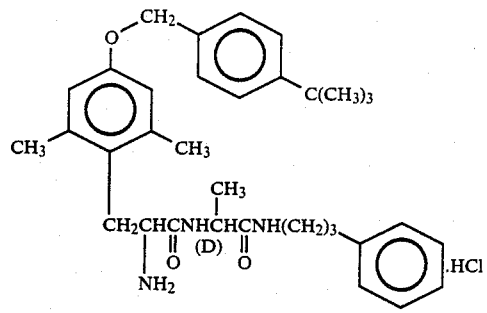

The product of Example 36, when exposed to the mixed anhydride condensation in Example 2, instead of O-Methyl-Boc-2,6-dimethyltyrosine, gave after workup, a mixture of diastereomers which was separated by column chromatography. Each diastereomer was then treated with dioxane/HCl/glacial acid as described in Example 2, to give the two diastereomers of the title compound.

(D,D): $C_{34}H_{45}N_3O_3 \cdot HCl \cdot \frac{1}{2}H_2O$ mw 589.22
Calc: C 69.31; H 8.04; N 7.13; Cl 16.02. Found: C 68.98; H 7.55; N 7.23; Cl 6.42.
NMR: alanyl methyl ∫1.15d.
$[\alpha]_D = -50.0°$.
(L,D) $C_{34}H_{45}N_3O_3 \cdot HCl \cdot \frac{1}{2}H_2O$ mw 589.22.
Calc: as (D,D). Found: C 69.25; H 7.93; N 7.36; Cl 6.14.
NMR: alanyl methyl ∫0.8d.
$[\alpha]_D = +102.4°$.

EXAMPLE 43

O[(4-cyanophenyl)methyl]-2,6-dimethyltyrosyl-N-(3-phenylpropyl)D-alaninamide, monohydrochloride

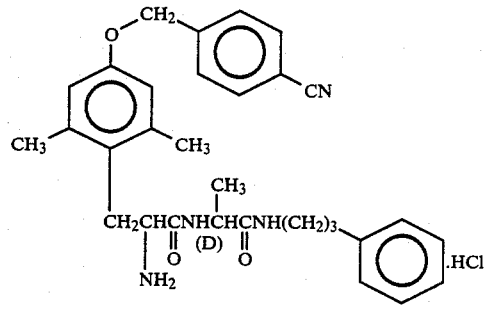

The product of Example 30, when exposed to the mixed anhydride condensation in Example 2, instead of O-Methyl-Boc-2,6-dimethyltyrosine, gave after workup, a mixture of diastereomers which was separated by column chromatography. Each diastereomer was then treated with dioxane/HCl/glacial acid as described in Example 2, to give the two diastereomers of the title compound having $[\alpha]_D$ of $-74.4°$ (D,D) and $+90.2°$ (L,D) in methanol.

(D,D): $C_{31}H_{36}N_4O_3 \cdot 1\frac{1}{8}HCl \cdot \frac{1}{2}H_2O$ mw 562.69.
Calc: C66.17; H 6.83; N 9.96; Cl 7.09. Found: C 65.80; H 6.67; N 9.84; Cl 6.86.

NMR: Alanine methyl group: ∫1.16d
(L,D) C₃₁H₃₆N₄O₃·HCl·½H₂O mw 553.62.
Calc: C 67.26; H 6.83; N 10.12; Cl 6.40 Found: C 66.96; H 6.96; N 10.09; Cl 6.59.
NMR: Alanine methyl group: ∫0.81d.

EXAMPLE 44

O-[(4-aminophenyl)methyl]-2,6-dimethyltyrosyl-N-(3-phenylpropyl)-D-alaninamide, monohydrochloride

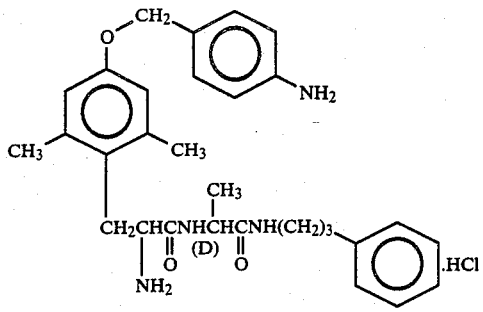

The title compound of Example 39 was treated with hydrogen in the presence of palladium on carbon in methanol. The mixture was filtered and concentrated to low volume. The resulting material was triturated with ether and dried to give the title compound having [α]_D of −60.0° in methanol (D,D).

C₃₀H₃₈N₄O₃·HCl·½H₂O mw 548.13.
Calc: C 65.74; H 7.36; N 10.22; Cl 6.47. Found: C 65.94; H 7.09; N 9.91; Cl 6.55.
NMR: alanyl methyl group ∫1.16d.

EXAMPLE 45

2R-[(cyclopropylmethyl)amino]-N-(3-phenylpropyl)-propanamide

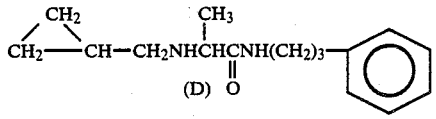

A mixture of (D)Alanylphenylpropylamide (0.825 g, 4.00 mmol), NaHCO₃ (1.00 g, 1.20 mmol), bromomethylcyclopropane (0.64 g, 4.74 mmol) and 10 ml Ethanol (2B) was heated at reflux for 8 hrs with stirring. The reaction mixture was partitioned between ethyl acetate and water. The organic layer was separated and dried over Na₂SO₄. The solvent was removed under reduced pressure and the resultant oil was purified by column chromatography on a Porasil column eluting with 3/96.8/0.2; MeOH/CHCl₃/NH₄OH. NMR: (CDCl₃) shift (D) Ala ∫1.28d, J=9 Hz. Cyclopropylmethyl; ∫0 to 0.25, complex, 2H ∫0.30 to 0.65, complex, 2H; ∫0.65 to 1.00, complex, 1H; ∫d of d ∫2.39 J₁=3.5 Hz, J₂=8 Hz.

A sample of the above product was dissolved in methanol and treated with sufficient HCl gas dissolved in 2-propanol to render acid. Anhydrous ether was added to the point of turbidity and the mixture cooled to 0°. The resultant solid was filtered and dried at reduced pressure under an inert atmosphere.

NMR: shift of (D)Ala methyl = ∫1.43(d)3H, J=9 Hz cyclopropyl methyl: ∫0.20 to 0.70, 4H, complex; ∫0.80 to 1.30, 1H, complex; 2.4 to 2.9, 2H hidden Analysis: Calc for C₁₆H₂₄N₂O·HCl: C 64.74; H 8.49; N 9.44; Cl 11.94. Found: C 64.63; H 8.37; N 9.44; Cl 12.11.

EXAMPLE 46

N-[(1,1-dimethylethoxy)carbonyl]-2,6-dimethyl-DL-tyrosyl-Nα-(cyclopropylmethyl)-N-(3-phenylpropyl)-D-alaninamide

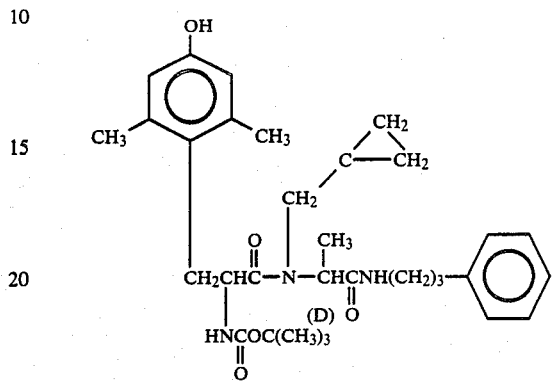

The title compound of Example 45 replaced (D)alanylphenylpropylamide in the mixed anhydride synthesis described in Example 2. It was reacted using Boc-2,6-dimethyltyrosine (2.97 g, 9.60 mmol), isobutylchloroformate (1.31 g, 9.60 mmol) and N-Methyl-morpholine (0.98 g, 9.60 mmol). Dimethylformamide replaced methylene chloride as the solvent. The reaction mixture was worked up as in Example 2 and the resultant foam (4.4 g) was purified by column chromatography on Merck silica eluting with 3% methanol-methylenechloride.

EXAMPLE 47

2,6-dimethyl-DL-tyrosyl-Nα-(cyclopropylmethyl)-N-(3-phenylpropyl)-D-alaninamide, monohydrochloride

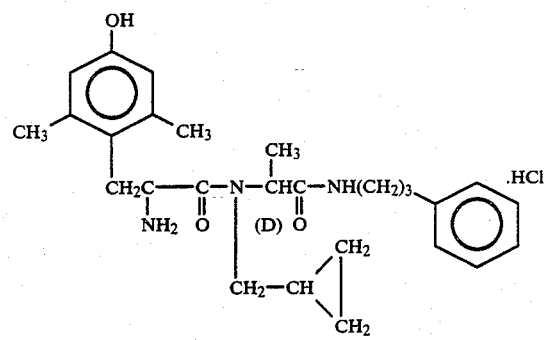

The product from Example 46 (0.51 g, 0.924 mmol) was treated with glacial acetic acid (5 ml) and 6.2N HCl/dioxane (1.36 ml) as described in Example 2 to give the desired 2,6-dimethyl(D,L) tyrosyl-N-cyclopropylmethyl-(D)-alanylphenylpropylamide hydrochloride.

C₂₇H₃₇N₃O₃·HCl·½H₂O MW 497.08.
Calc: C 65.24; H 7.91; N 8.45; Cl 7.13. Found: C 65.19; H 7.73; N 8.42; Cl 7.20.
[α]_D +13.6° NMR: (CDCl₃) cyclopropyl: ∫0 to 1.0 complex, 5H; ∫2.25 2H partially hidden by 2,6 Dimethyl groups (tyrosine) (D)ala methyl shifts ∫1.23 and 1.41 3H.

EXAMPLE 48

N-[(1,1-dimethylethoxy)carbonyl]-N-(2-propenyl)-D-alanine

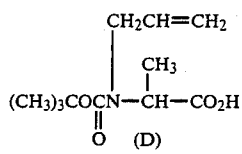

Allyl iodide (6.72 g, 40.0 mmol) replaced methyl iodide and Boc-(D)-alanine (1.89 g, 10.0 mmol) replaced Z-(D)alanine in the reaction of Example 15. They were reacted using sodium hydride (30.0 mmol, 50% suspension in mineral oil) and THF (30 ml). 2.27 g of oil was obtained using the procedure and work-up of Example 15.

NMR: (CDCl$_3$) alanylmethyl ∫1.45: N-allyl ∫3.70 to 4.00, 2H; 4.95 to 5.30, 2H; [α]$_D$ Methanol=43.3°.

EXAMPLE 49

1,1-dimethylethyl [1R-methyl-2-oxo-2-[(3-phenylpropyl)amino]ethyl](2-propenyl)carbamate

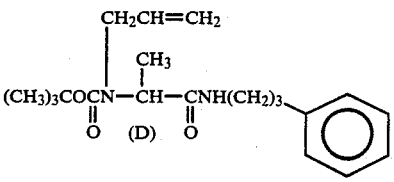

N-Allyl-Boc-(D)-alanine (Example 48) (9.58 g, 41.8 mmol) was treated with N-methyl morpholine (4.27 g, 41.8 mmol), isobutylchlorformate (5.71 g, 41.8 mmol) and 3-phenylpropylamine (5.65 g, 41.8 mmol) as described in Example 2 giving 18.83 g of a light oil.

NMR (CDCl$_3$) alanylmethyl ∫1.35; N-allyl; ∫3.70 to 3.90, 2H; 4.95 to 5.30, 2H; 5.50 to 6.10; 1H [α]$_D$ Methanol= +26.3°.

EXAMPLE 50

N-(3-phenylpropyl)-2R-(2-propenylamino)propanamide

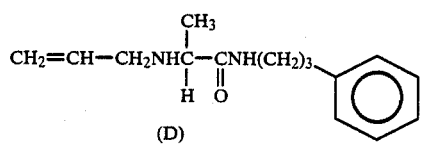

The product from Example 49 (13.83 g, 39.9 mmol) was treated with glacial acetic acid (100 ml) and 6.2N HCl/dioxane (58.7 ml) as decribed in Example 2 to give the desired N-allyl-D-alanylphenylpropylamide hydrochloride. This was converted to the base by dissolving in the minimal amount of water, treating with sufficient sold NaHCO$_3$ to render alkaline and extracting with methylene chloride. The extract was dried over Na$_2$SO$_4$ and the solvent removed under reduced pressure to give 8.98 g of a light oil.

EXAMPLE 51

N[(1,1-dimethylethoxy)carbonyl]-2,6-dimethyltyrosyl-N-(3-phenyl propyl)-Nα-(2-propenyl)-D-alaninamide

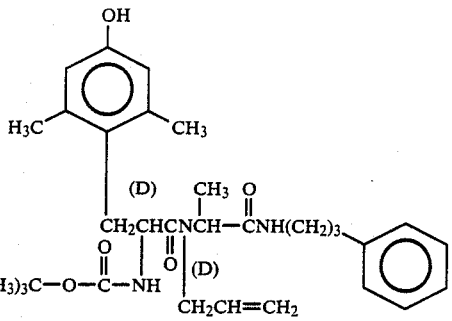

N-Allyl-(D)-alanylphenylpropylamide (5.00 g, 20.3 mmol) replaced (D) alanyl-phenylpropylamide in the mixed anhydride synthesis described in Example 2. It was reacted using Boc-2,6-dimethyl-tyrosine (6.28 g, 20.3 mmol) N-methyl morpholine (2.05 g, 20.3 mmol) and isobutylchloroformate (2.77 g, 20.3 mmol). Dimethylformamide replaced CH$_2$Cl$_2$ as the solvent. The reaction mixture was worked up as in Example 2 and the resultant oil (10.62 g) was purified by column chromatography on Woelm silica eluting with 3 to 5% methanol-methylene chloride and the diasteromers were separated:

NMR: (CDCl$_3$) First isomer from the column: (D) alanyl methyl ∫0.44 and 1.00 to 1.50 (rotamers) 3H; N-allyl (propenyl) ∫3.50 to 3.80, 2H; 4.80 to 5.25, 2H; 5.25 to 5.75 1H.

NMR(CDCl$_3$) Second isomer from the column; D-alanyl methyl ∫1.00 to 1.50 (rotamers) 3H; N-allyl (propenyl) 3.50 to 3.80, 2H; 4.80 to 5.21, 2H; 5.25 to 5.75 1H.

EXAMPLE 52

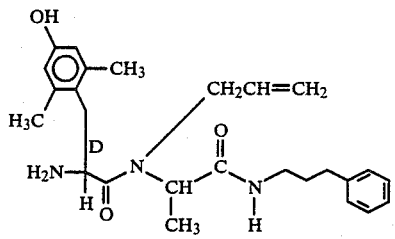

1.00 g of the fast moving isomer from Example 51 was treated with glacial acetic acid (6 ml) and 6.2N Hcl/dioxan (2.7 ml) as described in Example 2 to give the desired (D) 2,6-dimethyltyrosyl-N-(3-phenylpropyl-Nα-[2-propenyl]-D-alaninamide hydrochloride.

C$_{26}$H$_{35}$N$_3$O$_3$.HCl.½H$_2$O MW 483.05.

Calc: C,64.65; H, 7.72; N, 8.70; Cl −7 34. Found: C, 64.49; H, 7.61; N, 8.74; Cl −7.45

[α]$_D$.

NMR: (DMSO d$_6$) ISO F-(D)alanyl methyl ∫0.47+1.13 (Rotamers), 3H; N-allyl (propenyl) ∫4.50 to 5.50, 2H 5.25–5.85, 1H.

The slower moving fraction was treated as described directly above to yield the L,D isomer.

C$_{26}$H$_{35}$N$_3$O$_3$.HCl.½H$_2$O mw 483.05.

Calc: C 64.65 H 7.72; N 8.70; Cl 7.34. Anel: C 64.87; H 7.56; N 8.60; Cl 7.66.

$[\alpha]_D = +117.9°$.
NMR: (D)ala methyl $f = 1.03d$

EXAMPLE 53

Phenylmethyl 4-[[2,6-dimethyl-4-(phenylmethoxy)phenyl]methyl]-5-oxo-2-phenyl-3-oxazolidinecarboxylate 2,6-dimethyltyrosine hydrochloride (20.0 g) was dissolved in water (1 liter). The pH was adjusted to 8.5 (10% NaOH in H$_2$O), and benzylchloroformate (14.3 g) was added in one portion. The pH was maintained between 7 and 8 with the aqueous NaOH for two hours. The reaction mixture was then acidified (Conc HCl) and extracted with ethyl acetate. The aqueous layer was saturated with NaCl, and then extracted three times with ethyl acetate. The organic fractions were combined, dried (Na$_2$SO$_4$), filtered, and stripped to an oil. This oil was triturated with ether/hexane, giving a solid. The solid was ground up (mortar & pestle) and dried overnight at 42° and 110 torr.

A portion of the resulting N-carbobenzoxy (Z)-2,6-dimethyltyrosine (15 g, 43.7 mmol) was dissolved in dimethylformamide DMF (200 ml) and treated with benzyl bromide (29.9 g, 20.0 ml, 174.7 mmol) and potassium carbonate (18.1 g, 131.1 mmol) at room temperature for 16 hr. The reaction mixture was diluted to 1.7 liter with H$_2$O, and then extracted twice with CH$_2$Cl$_2$. The organic fractions were combined, dried (MgSO$_4$), filtered and stripped to an oil. This oil was subjected to column chromatography on slica gel, using ethyl acetate-hexane eluent. The major product was N-Z-2,6-dimethyltyrosine benzyl ester. This material (11.1 g, 25.6 mmol) was used directly in the next step. Sodium hydride dispersion in mineral oil (28.2 mmol) was washed with petroleum ether and suspended in DMF (200 ml). All of the N-Z-2,6-dimethyltyrosine benzyl ester was added thereto. After 10 min of stirring, benzyl bromide (3.20 ml, 4.60 g, 26.9 mmol) was added all at once. The mixture was stirred 16 hr, and then worked up as described above, giving 13 g of dibenzylated product.

The resulting O-benzyl-N-Z-2, 6-dimethyltyrosine benzyl ester was hydrolyzed to the free acid with methanolic sodium hydroxide as described in Example 1, giving 12.1 g of O-benzyl-N-Z-2,6-dimethyltyrosine. This acid (12 g, 27.7 mmol) was placed in a 500 ml round bottom single neck flask fitted with a Soxhlet extractor which was filled with 5A molecular sieves (8–12 mesh beads). The flask was also charged with 1,1,1-trichloroethane (350 ml), benzaldehyde (5.62 ml, 5.86 g, 55.4 mmol), and toluene-sulfonic acid monohydrate (5.27 g, 27.7 mmol). The flask was immersed in an oil bath (bath temperature 120°) and the mixture was refluxed for 16 hr. The reaction was then cooled and the mixture was washed with sat NaHCO$_3$. The aqueous wash was back-washed twice wth CH$_2$Cl$_2$. All the organic fractions were combined, dried (MgSO$_4$), filtered, stripped, and subjected to column chromatography on silica with eluents of ethyl acetate-hexane. The title compound was isolated as a solid which was washed with ethanol and then ether. NMR: aromatic proton $f$ 4.21 m, benzyhydryl proton under benzyl peaks $f$ 4.99. Integration shows three benzyl (idene) groups.

EXAMPLE 54 phenylmethyl 4-[[2,6-dimethyl-4-(phenylmethoxy)phenyl]methyl]-4-methyl-5-oxo-2-phenyl-3-oxazolidinecarboxylate A 500 ml round bottom flask fitted with a magnetic stirrer, thermometer, dropping funnel, and y-tube (connected to an N$_2$ inlet and a drying tube outlet) was charged with dry THF (150 ml), which was cooled (dry ice bath) to $-60°$. A solution of potassium hexamethyldislazane in toluene (0.653M, 21.0 ml, Callery Chemical Company, Callery, Pa.) was added all at once. The solution was cooled back to $-70°$, and a solution of the title compound of Example 53 (5.5 g, 10.6 mmol) in THF (100 ml) was added dropwise rapidly, keeping the reaction temperature at or below $-62°$. The mixture was then stirred in the cold bath for 30 min, and the cold bath was then removed. Stirring at room temperature for another 30 min elevated the reaction tempature to $-12°$. The reaction mixture was then re-immersed in the cold bath, and the temperature returned to $-70°$. Methyl iodide (1.05 ml, 2.40 g, 16.9 mmol) was added al at once, and after another 10 min the cold bath was removed. The reaction mixture was permitted to warm to room temperature, and 3 hr after removal of the cold bath the mixture was partitioned between a mixture of H$_2$O (200 ml), 0.5N KHSO$_4$ (50 ml), saturated brine (200 ml) and ether (200 ml). The aqueous phase was washed with ether, the organic fractions were combined, dried (MgSO$_4$), filtered, and stripped to an oil. The oil was applied to silica gel column chromatography on using ethyl acetate-hexane eluent, giving the title compound. NMR: $\alpha$ methyl group at $f$ 2.71 A, 3 protons.

EXAMPLE 55

$\alpha$,2,6-trimethyl-4-(phenylmethoxy)-$\alpha$-[[(phenylmethoxy)carbonyl]amino]benzenepropanoic acid The title compound of Example 54 (2.42 g) was dissolved in 5 ml of 1:1 CH$_2$Cl$_2$: methanol, and added to methanolic NaOH (1N, 100 ml). After 3 hr of stirring, the mixture was concentrated to 75 ml, diluted to 500 ml with water, and extracted twice with ether to remove non-acidic contaminants. The aqueous phase was made acidic with 0.5N KHSO$_4$, and then extracted four times with CH$_2$Cl$_2$. The CH$_2$Cl$_2$ fractions were combined, dried (MgSO$_4$), filtered, and stripped to give the title compound (1.75 g). NMR:$\alpha$ methyl group at $f$ 2.75.

EXAMPLE 56

$\alpha$,2,6-trimethyl-N-[(phenylmethoxy)carbonyl]-O-(phenylmethyl) tyrosyl-N-(3-phenylpropyl)alaninamide The title compound of Example 55 was reacted uuder mixed anhydride conditions as described in Example 2 to give the Z-protected dipeptide amide (acid 1.75 g, 3.91 mmol; N-methylmorpholine 0.42 g, 4.11 mmol; isobutylchloroformate 0.53 ml, 4.03 mmol; (D)-alanylphenylpropylamide 0.85 g, 4.11 mmol). The product, 2.32 g, was subjected to column chromatography on silica gel, using ethanol: methyl tert-butyl ether: ammonium hydroxide eluent. The two diastereomers were thus separated, giving a faster-emerging and a slower-emerging isomer.

EXAMPLE 57

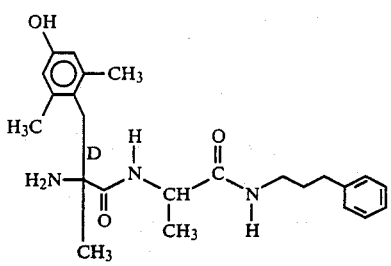

α,2,6 trimethyl D-tyrosyl-N-(3-phenylpropyl) D-alaninamide

The more rapidly emerging title isomer of Example 56 (1.0 g) was hydrogenolyzed in methanol with a palladium black catalyst (0.31 g) at room temperature for 17 hr at 60 psi of hydrogen. The mixture was filtered to remove the catalyst, re-filtered through to remove fines particles, and stripped. The residue was dissolved in ethanol-water-methanol, filtered, reduced in volume with a nitrogen stream, and lyophilized to give the title compound, the D, D, isomer. NMR: α-methyl group at ∫2.11 and 2.25 for two rotamers; alanyl methyl at ∫1.21 d, $J=7Hz.[\alpha]_D = -23.2°$. For $C_{24}H_{33}N_3O_3 \cdot \frac{1}{4}H_2O$ (mw 416.05):

Calc: C, 69.29; H, 8.12; N, 10.10. Found: C, 69.24; H, 8.11; N, 9.81.

EXAMPLE 58

α2,6-trimethyl-L-tyrosyl-N-(3-phenylpropyl)-D-alaninamide

The more slowly emerging title isomer of Example 565 was treated as described in example 56 to give the title compound, the L, D isomer.

NMR: ∫1.10 d, $J=7Hz.[\alpha]_D+90.1°$.

For $C_{24}H_{33}N_3O_3$ (mw 411.54): Calc: C, 70.04; H, 8.08; N, 10.21. Found: C, 70.41; H, 7.95; N, 10.21.

EXAMPLE 59

Analgesic properties of the substituted dipeptide amides

The receptor binding and biological properties of the following compounds of this invention are illustrated in Table 1 utilizing the previously described opiate binding and writhing assay. The standard screening dose for the writhing assay was 10 mg/kg s.c. and p.o. The standard screening dose for the opiate binding assay was $10^{-5}$ Molar.

TABLE 1

| | ANALGESIC PROPERTIES | | |
|---|---|---|---|
| Example | Opiate[a] Binding | Writhing Mouse[b] Subc. | Oral |
| 2 | $2.9 \times 10^{-7}$ | Active | Active |
| 3 | $4.2 \times 10^{-7}$ | Active | Active |
| 4 | $7.5 \times 10^{-8}$ | Active | Active |
| 5 | $1.3 \times 10^{-7}$ | Active | Inactive |
| 6 | $4.7 \times 10^{-8}$ | Inactive | Inactive |
| 11 | $6.1 \times 10^{-7}$ | Active | Active |
| 9 | Inactive | Active | Active |
| 12 | $3.6 \times 10^{-6}$ | Active | Active |
| 13 | $1.8 \times 10^{-6}$ | Active | Inactive |
| 14 | $1.4 \times 10^{-7}$ | Active | Inactive |
| 15 | $6.0 \times 10^{-10}$ | Active | Active |
| 16 | $3.0 \times 10^{-7}$ | Active | Inactive |
| 23 | $7.6 \times 10^{-9}$ | Active | Active |
| 25 | $2.0 \times 10^{-6}$ | Active | Inactive |
| 27 | $3.6 \times 10^{-7}$ | Active | Active |
| 28 | $2.2 \times 10^{-8}$ | Active | Active |

[a] = $IC_{50}$ expressed as moles/liter
[b] = Active refers to the effect of the screening dose (10 mg/kg).

What is claimed is:

1. A compound of the formula:

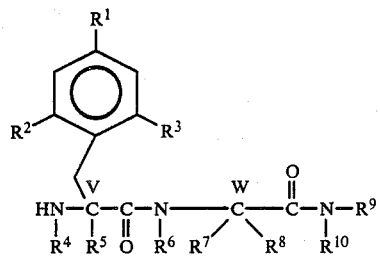

and the pharmaceutically acceptable acid addition salts thereof wherein $R^1$ is lower alkoxy or —O—$(CH_2)_n$—phenyl where the phenyl may be optionally substituted with halogen, —$NO_2$, —CN, —$NH_2$ or lower alkyl wherein n is 1 to 4; $R^2$ and $R^3$ represent lower alkyl, halogen, lower alkoxy or one of $R^2$ or $R^3$ is hydrogen and the other is lower alkyl, lower alkoxy, or halogen; $R^4$, $R^5$, $R^7$, $R^8$ and $R^9$ represent hydrogen or lower alkyl, $R^6$ represents hydrogen, lower alkyl, lower alkenyl, or —$(CH_2)_m$—cycloalkyl wherein m is 1 to 4 and the cycloalkyl has 3 to 8 carbon atoms; $R^{10}$ is —$(CH_2)_p$—phenyl wherein p is 1 to 4; and v represents an asymmetric carbon that may be racemic or have the D or L Configuration; w represents an asymmetric carbon when $R^7$ and $R^8$ are not the same that may be racemic or have the D or L configuration; and $R_1$ may be hydroxy when at least one of $R^4$, $R^5$, $R^6$, or $R^9$ is lower alkyl.

2. A compound according to claim 1 of the formula:

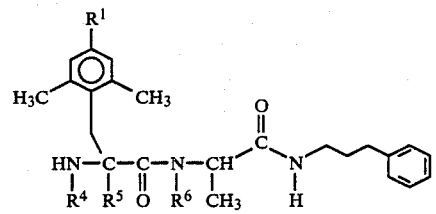

and the pharmaceutically acceptable acid addition salts thereof wherein both $R^1$ is lower alkoxy or —O—$(CH_2)_n$—phenyl with the phenyl optionally substituted with halogen, —$NO_2$, —CN, —$NH_2$, or lower alkyl wherein n is 1 to 4; $R^4$, $R^5$, and $R^6$ are hydrogen or lower alkyl; and the optical isomer thereof.

3. The compound, according to claim 2, which is O-ethyl-2,6-dimethyltyrosyl-N-(3-phenylpropyl)-D-alaninamide, and the acetate or hydrochloride.

4. The compound according to claim 2, which is 2,6,dimethyl-O-(1-methylethyl)tyrosyl-N-(3-phenylpropyl)-D-alaninamide, hydrochloride.

5. A compound according to claim 2, which is N,O2,6,-tetramethyltyrosyl-N-(3-phenylpropyl)-D-alaninamide, hydrochloride.

6. A compound according to claim 2, which is N,O,2,6,-tetramethyltyrosyl-N-(3-phenylpropyl)-D-alaninamide, hydrochloride.

7. A compound according to claim 2, which is N,2,6-trimethyl-O-(phenylmethyl)-tyrosyl-N-(3-phenylpropyl)-D-alaninamide, hydrochloride.

8. A compound according to claim 2, which is 2,6-dimethyl-O-(phenylmethyl)-tyrosyl-N-(3-phenylpropyl)-D-alaninamide, hydrochloride.

9. A compound according to claim 2, which is O-[(4-chlorophenyl)methyl]-2,6-dimethyltyrosyl-N-(3-phenylpropyl)-D-alaninamide, hydrochloride.

10. A compound according to claim 2, which is 2,6-dimethyl-O-[(2-methylphenyl)methyl]tyrosyl-N-(3-phenylpropyl)-D-alaninamide, hydrochloride.

11. A compound according to claim 2, which is 2,6-dimethyl-O-[(4-nitrophenyl)methyl]tyrosyl-N-(3-phenylpropyl)-D-alaninamide, hydrochloride.

12. A compound according to claim 2, which is O-[(4-fluorophenyl)methyl]-2,6-dimethyltyrosyl-N-(3-phenylpropyl)-D-alaninamide, hydrochloride.

13. A compound according to claim 2, which is 2,6-dimethyl-O-[(4-methylphenyl)methyl]tyrosyl-N-(3-phenylpropyl)-D-alaninamide, hydrochloride.

14. A compound according to claim 2, which is O-[[4-(1,1-dimethylethyl)phenyl]methyl]-2,6-dimethyltyrosyl-N-(3-phenylpropyl)-D-alaninamide, hydrochloride.

15. A compound according to claim 2, which is O-[(4-cyanophenyl)methyl]-2,6-dimethyltyrosyl-N-(3-phenylpropyl)-D-alaninamide, hydrochloride.

16. A compound according to claim 1 of the formula

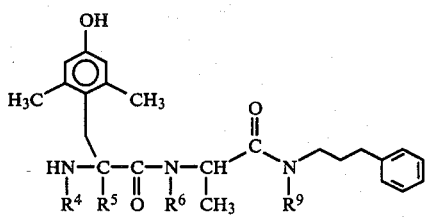

wherein one of $R^4$, $R^5$, $R^6$ and $R^9$ are lower alkyl and the other are hydrogen.

17. A compound according to claim 16 which is N,2,6-trimethyltyrosyl-N-(3-phenylpropyl)-D-alaninamide, hydrochloride.

18. A compound according to claim 16 which is 2,6-dimethyl-DL-tyrosyl-N$\alpha$-methyl-N-(3-phenylpropyl)-D-alaninamide, hydrochloride.

19. A compound according to claim 16, which is 2,6-dimethyl-DL-tyrosyl-N-methyl-N-(3-phenylpropyl)-D-alaninamide, hydrochloride.

20. A compound according to claim 16 which is $\alpha$,2,6 trimethyl D-tyrosyl-N-(3-phenylpropyl) D-alaninamide.

21. A compound according to claim 16 which is $\alpha$,2,6-trimethyl-L-tyrosyl-N-(3-phenylpropyl)-D-alaninamide.

22. A compound of the formula

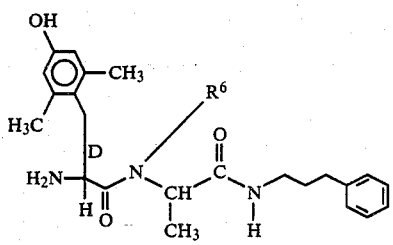

and the pharmaceutically acceptable acid addition salts thereof wherein $R^6$ is 2-propenyl or cyclopropylmethyl.

23. A compound according to claim 22 which is 2,6-dimethyl-DL-tyrosyl-N$\alpha$-(cyclopropylmethyl)-N-(3-phenylpropyl)-D-alaninamide, hydrochloride.

24. A compound according to claim 22 which is 2,6-dimethyltyrosyl-N-(3-phenylpropyl-N$\alpha$-[2-propenyl]-D-alaninamide, hydrochloride.

25. The compound according to claim 1 which is 2,6,dichlorotyrosyl-N-(3-phenylpropyl)-D-alaninamide, hydrochloride.

26. 2,4,6-trimethylphenylalanyl-N-(3-phenylpropyl)-D-alaninamide, hydrochloride.

* * * * *

UNITED STATES PATENT AND TRADEMARK OFFICE
CERTIFICATE OF CORRECTION

PATENT NO. : 4,760,180

DATED : July 26, 1988

INVENTOR(S) : Pitzele, et. al.

It is certified that error appears in the above-identified patent and that said Letters Patent is hereby corrected as shown below:

Column 2, the second structure, that part of the structure reading

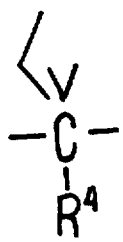   should read   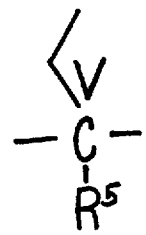

Column 10, line 3, reading "(2.68 g, 19 39 mmol)" should read -- (2.68 g, 19.39 mmol) --.

Column 10, line 22, reading "-11.8°" should read -- +11.8° --.

Column 11, line 65, reading "N-methylmorphonline (3.08 g. 30.4 mmol), isobutyl" should be deleted.

UNITED STATES PATENT AND TRADEMARK OFFICE
CERTIFICATE OF CORRECTION

PATENT NO. : 4,760,180
DATED : July 26, 1988
INVENTOR(S) : Pitzele, et. al.

It is certified that error appears in the above-identified patent and that said Letters Patent is hereby corrected as shown below:

Column 23, line 5, reading "$C_{24}H_{33}N_3O_2 \cdot 1/4 H_2O$" should read -- $C_{24}H_{33}N_3O_2 \cdot HCl \cdot 1/4 H_2O$ --.

Column 32, the first structure, that part of the structure reading

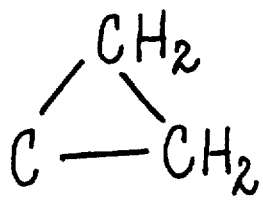  should read  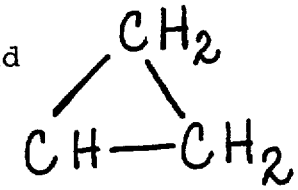

Signed and Sealed this

Twenty-first Day of November, 1989

Attest:

JEFFREY M. SAMUELS

Attesting Officer     Acting Commissioner of Patents and Trademarks